United States Patent
Shimada et al.

(10) Patent No.: US 10,859,583 B2
(45) Date of Patent: Dec. 8, 2020

(54) FECES SAMPLING CONTAINER, METHOD FOR MEASURING COMPONENTS IN FECES SAMPLE, METHOD FOR STABILIZING COMPONENTS IN FECES SAMPLE, AND METHOD FOR STORING FECES SAMPLE

(71) Applicant: KYOWA MEDEX CO., LTD., Tokyo (JP)

(72) Inventors: Yasumasa Shimada, Tokyo (JP); Kohei Tsuchiya, Sunto-gun (JP); Yuki Kaname, Sunto-gun (JP)

(73) Assignee: HITACHI CHEMICAL DIAGNOSTICS SYSTEMS CO., LTD., Tokyo (JP)

( * ) Notice: Subject to any disclaimer, the term of this patent is extended or adjusted under 35 U.S.C. 154(b) by 243 days.

(21) Appl. No.: 16/060,518

(22) PCT Filed: Dec. 13, 2016

(86) PCT No.: PCT/JP2016/005120
§ 371 (c)(1),
(2) Date: Jun. 8, 2018

(87) PCT Pub. No.: WO2017/104132
PCT Pub. Date: Jun. 22, 2017

(65) Prior Publication Data
US 2019/0011462 A1    Jan. 10, 2019

(30) Foreign Application Priority Data
Dec. 16, 2015 (JP) ................... 2015-245389

(51) Int. Cl.
*G01N 1/04* (2006.01)
*G01N 33/72* (2006.01)
(Continued)

(52) U.S. Cl.
CPC ............. *G01N 33/721* (2013.01); *G01N 1/04* (2013.01); *G01N 33/48* (2013.01); *A61B 10/0038* (2013.01)

(58) Field of Classification Search
CPC ...... A61B 10/0038; G01N 1/04; G01N 33/48; G01N 33/721
See application file for complete search history.

(56) References Cited

U.S. PATENT DOCUMENTS

2006/0188939 A1* 8/2006 Gao ................... A61B 10/0038
435/7.1
2009/0215159 A1* 8/2009 Kirby ..................... B01L 3/502
435/287.2
(Continued)

FOREIGN PATENT DOCUMENTS

| JP | 5-25358 U | 4/1993 |
| JP | 5-93722 A | 4/1993 |

(Continued)

OTHER PUBLICATIONS

Extended Search Report dated Jul. 4, 2019, issued in counterpart EP Application No. 16875121.2 (12 pages).
(Continued)

*Primary Examiner* — Jennifer Wecker
(74) *Attorney, Agent, or Firm* — Westerman, Hattori, Daniels & Adrian, LLP

(57) ABSTRACT

A feces sampling container having an increased storage stability of a component in a feces sample such as hemoglobin to enable the measurement of a component in a feces sample with a small amount of feces collected. The container includes a container body, and a feces sampling stick having a gripping part on one side and a stick part on the other side, the stick part having a feces sampling part in the vicinity of the tip, wherein the container body comprises an opening part through which the feces sampling part of the
(Continued)

feces sampling stick is inserted, and a feces container chamber in which a desiccant is enclosed, wherein the feces sample held by the feces sampling part is dried by a contact of the feces sampling part, which is inserted through the opening part and holding the feces sample, with the desiccant.

19 Claims, 6 Drawing Sheets

(51) Int. Cl.
  *G01N 33/48* (2006.01)
  *A61B 10/00* (2006.01)

(56) References Cited

U.S. PATENT DOCUMENTS

| | | | |
|---|---|---|---|
| 2011/0243816 A1* | 10/2011 | Shimada | A61B 10/0038 422/547 |
| 2012/0051974 A1 | 3/2012 | Wang | |
| 2012/0125125 A1 | 5/2012 | Li et al. | |
| 2014/0038172 A1* | 2/2014 | De La Rosa | G01N 1/30 435/5 |
| 2016/0256136 A1 | 9/2016 | Saito et al. | |

FOREIGN PATENT DOCUMENTS

| | | |
|---|---|---|
| JP | 5-126827 A | 5/1993 |
| JP | 5-249847 A | 9/1994 |
| JP | 2012-518175 A | 8/2012 |
| JP | 2013-500478 A | 1/2013 |
| JP | 2015-34806 A | 2/2015 |
| JP | 2015-75435 A | 4/2015 |
| WO | 00/51496 A1 | 9/2000 |
| WO | 2010/067534 A1 | 6/2010 |

OTHER PUBLICATIONS

Wasser, S.K. et al., "Techniques for application of faecal DNA methods to field studies of Ursids", Molecular Ecology, Jan. 1, 1997, vol. 6, pp. 1091-1097, Cited in the Extended EP Search Report dated Jul. 4, 2019.

Haag, Taiana et al., "Development and testing of an optimized method for DNA-based identification of jaguar (Panthera onca) and puma (Puma concolor) faecal samples for use in ecological and genetic studies", Genetica, Jan. 10, 2009, vol. 136, No. 3, pp. 505-512, Cited in Extended EP Search Report dated Jul. 4, 2019.

Regnaut, Sebastien et al., "Genotyping faeces reveals facultative kin association on capercaillie's leks", Conservation Genetics, Feb. 21, 2006, vol. 7, No. 5, pp. 665-674, Cited in Extended EP Search Report dated Jul. 4, 2019.

Murphy, Melanie A. et al., "Quantitative evaluation of fecal drying methods for brown bear DNA analysis", Wildlife Society Bulletin, Jan. 1, 2000, vol. 28, No. 4, pp. 951-957, Cited in Extended EP Search Report dated Jul. 4, 2019.

Nechvatal, Jordan M. et al., "Fecal collection, ambient preservation, and DNA extraction for PCR amplification of bacterial and human markers form human feces", Journal of Microbiological Methods, Elsevier, Nov. 21, 2007, vol. 72, No. 2, pp. 124-132, Cited in Extended EP Search Report dated Jul. 4, 2019.

Notification of Transmittal of Translation of the International Preliminary Report on Patentability (Form PCT/IB/338) issued in counterpart International Application No. PCT/JP2016/005120 dated Jun. 28, 2018, with Forms PCT/IB/373 and PCT/ISA/237. (7 pages).

* cited by examiner

[Figure 1]
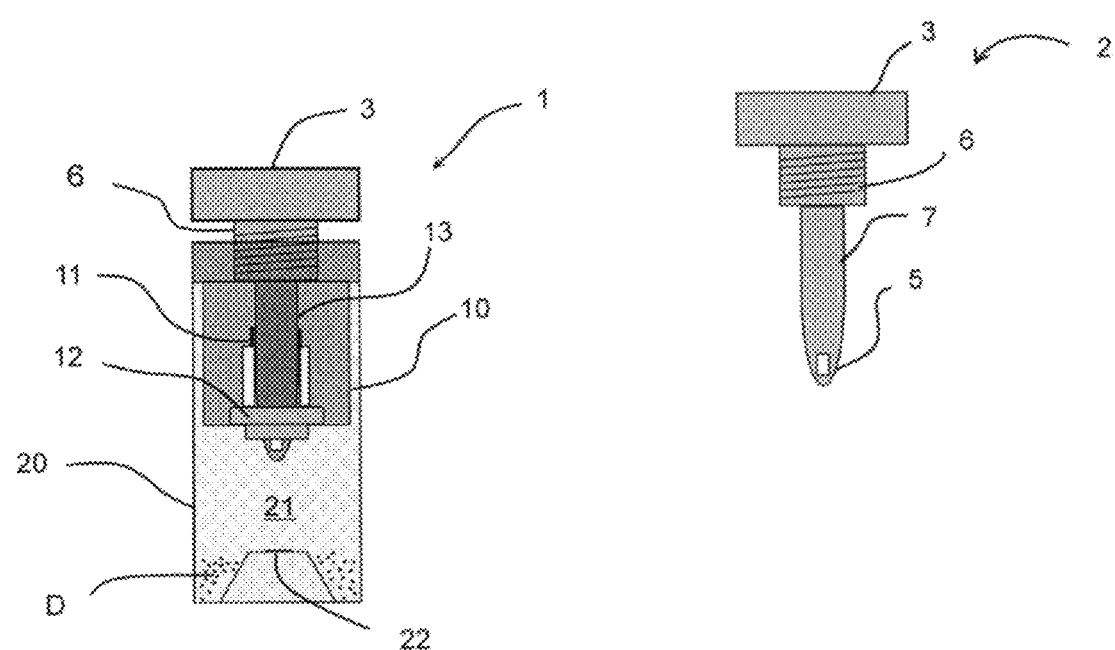

[Figure 2]
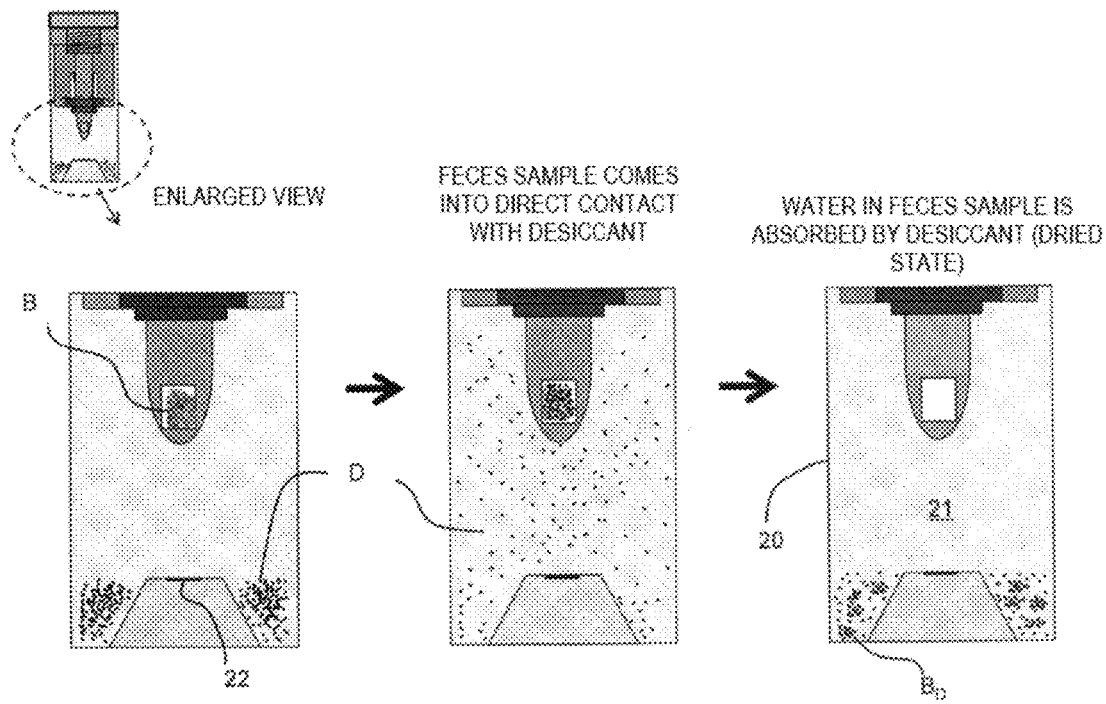
[Figure 3]
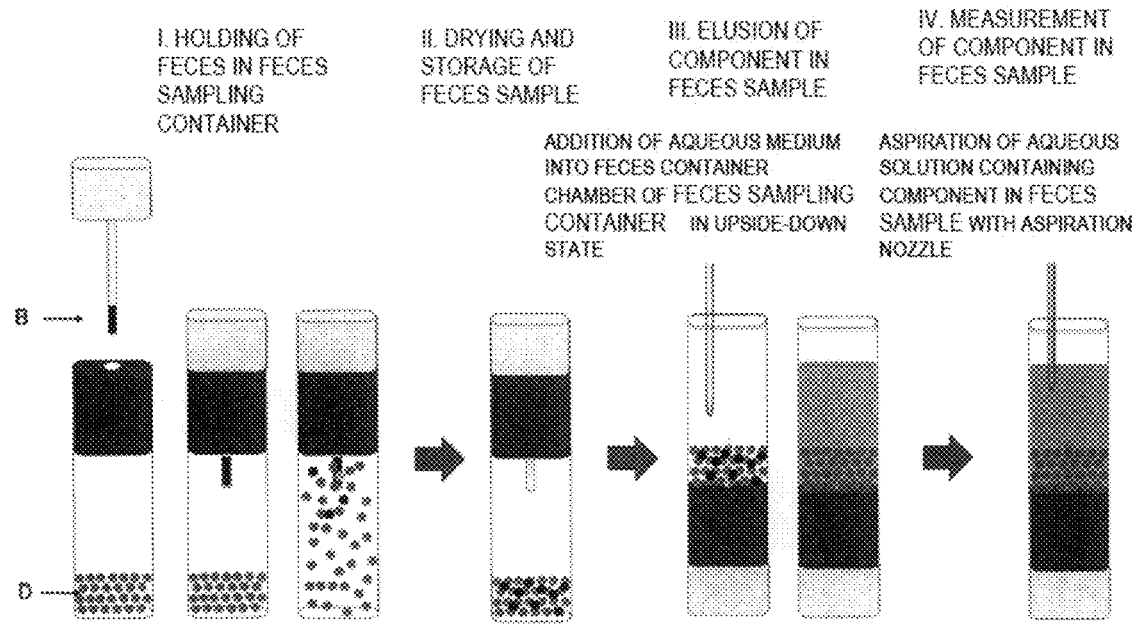

[Figure 5]
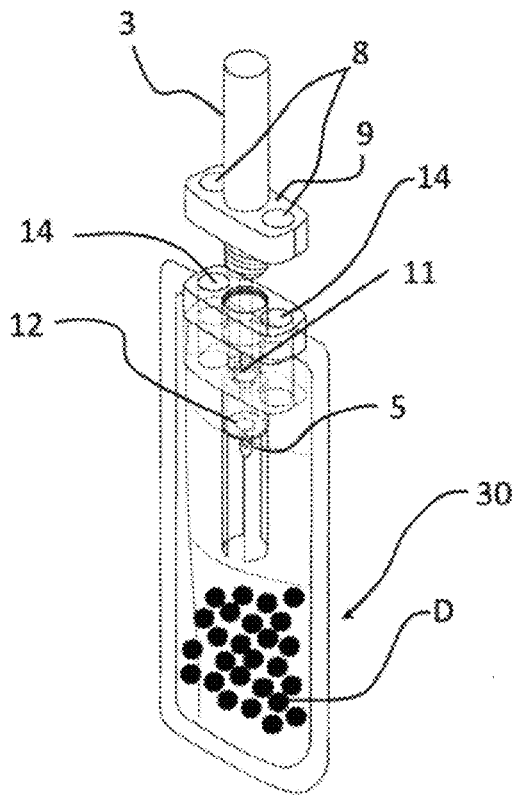
[Figure 6]
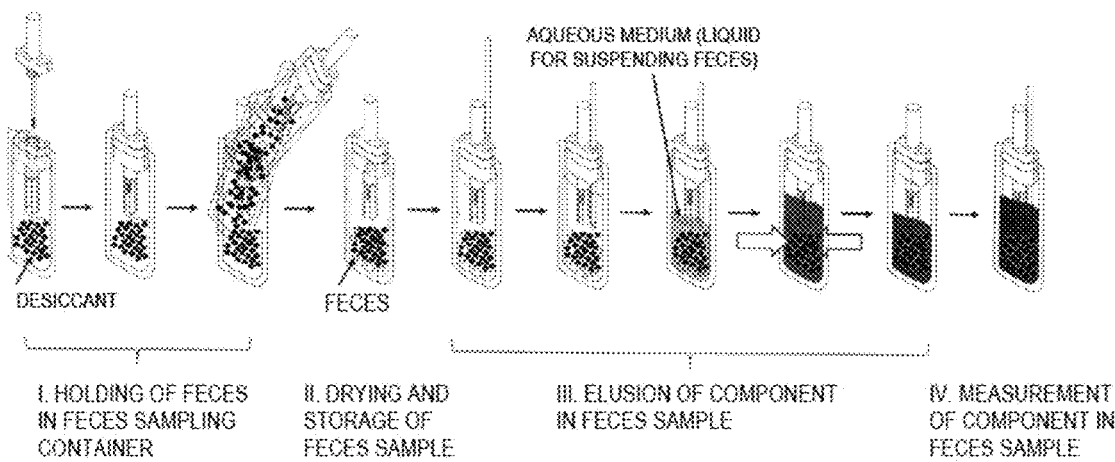

[Figure 7]
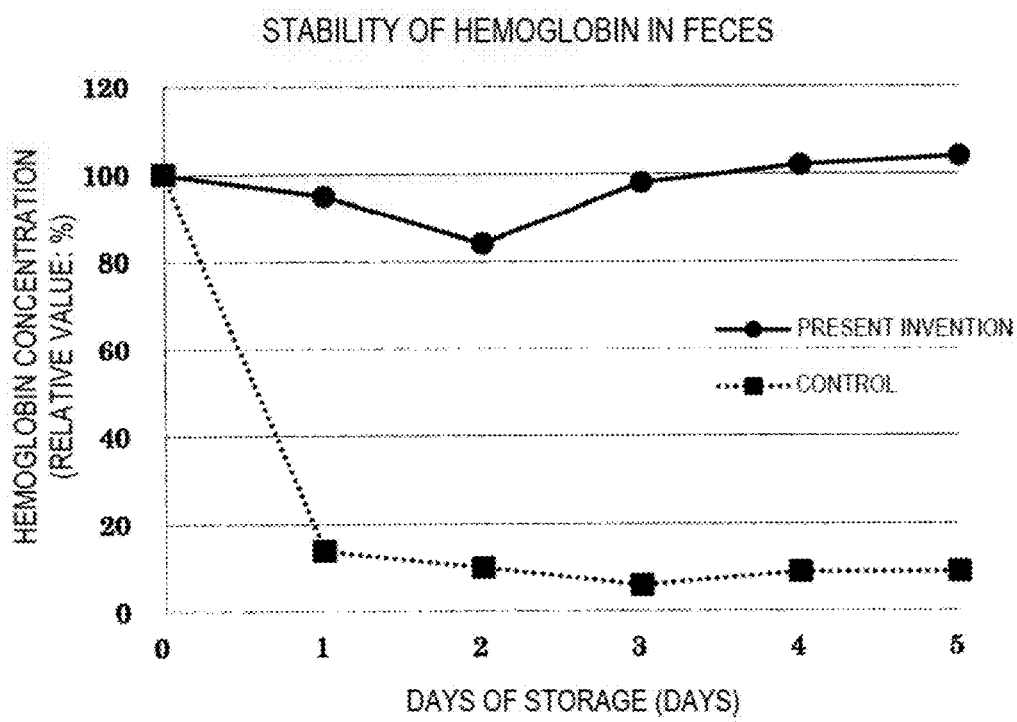
[Figure 8]
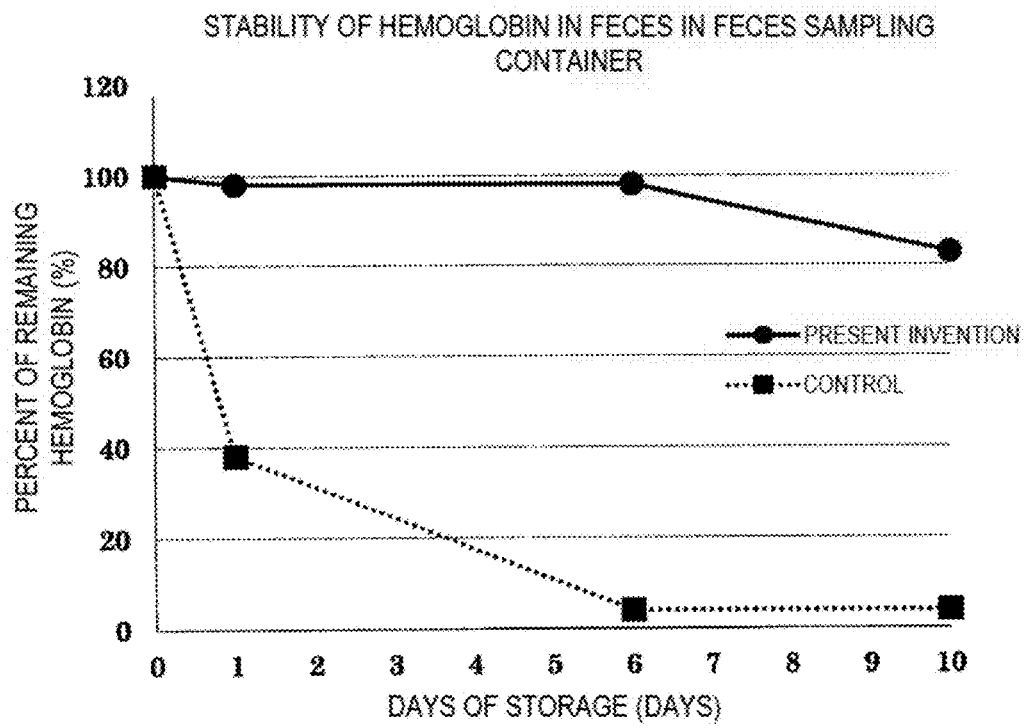

[Figure 9]
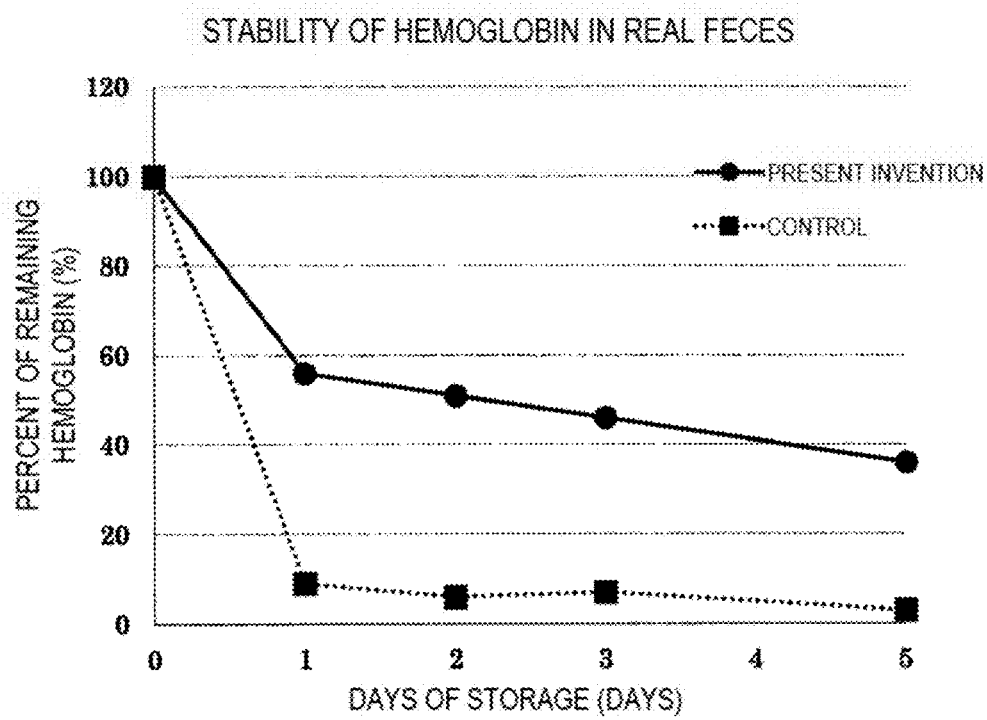
[Figure 10]
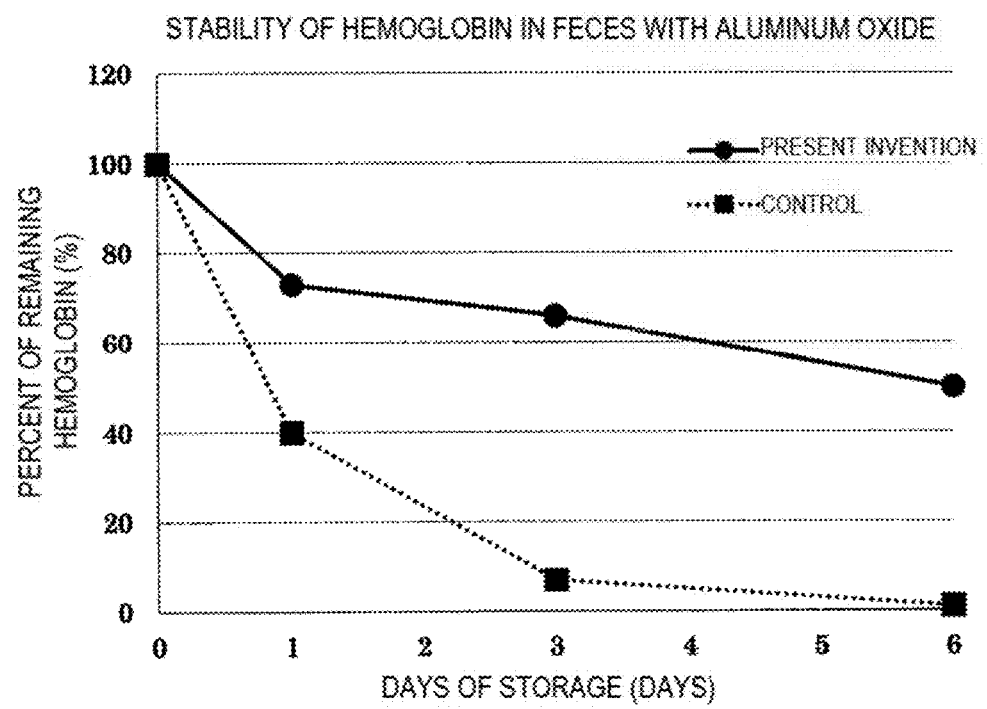

FECES SAMPLING CONTAINER, METHOD FOR MEASURING COMPONENTS IN FECES SAMPLE, METHOD FOR STABILIZING COMPONENTS IN FECES SAMPLE, AND METHOD FOR STORING FECES SAMPLE

TECHNICAL FIELD

The present invention relates to a feces sampling container, a method for measuring a component in a feces sample, a method for stabilizing a component in a feces sample, and a method for storing a feces sample.

BACKGROUND ART

The so-called fecal occult blood test, which examines hemoglobin in feces evacuated from animals including humans, is often used in clinical test since it is very useful for the diagnosis of various diseases such as tumors in lower gastrointestinal tracts including large intestine. For the test, feces need to be collected quantitatively and then suspended in a suitable buffer solution. In order to achieve these requirements by using simple, hygienic, and accurate means and make it possible to hygienically store and transport the collected feces, various feces sampling containers have been developed and a large number of such units have been reported (see patent document 1).

However, in most of feces sampling containers in practical use, the feces container chamber is formed as a feces-suspending liquid container part. Meanwhile, known examples in which the feces container chamber is formed as a feces drying part instead of a feces suspending liquid container part include a method for storing a collected feces sample applied on a filter paper in a non-water permeable closed packing containing a drying material to maintain stability of hemoglobin in the feces (see patent document 2) and a feces collecting container with a desiccant, comprising of a container body and a cover body, wherein the container body is compartmentalized with a partition into a desiccant storage chamber containing a desiccant and a stick reception chamber that can take in at least a sample-attaching part of a feces sampling stick, the stick reception chamber and the desiccant storage chamber communicate with each other, and the container body can be closed airtight with the cover body (see patent document 3).

PRIOR ART DOCUMENTS

Patent Documents

Patent Document 1: WO2010/067534
Patent Document 2: Japanese unexamined Patent Application Publication No. 5-126827
Patent Document 3: Japanese unexamined Patent Application Publication No. 6-249847

SUMMARY OF THE INVENTION

Object to be Solved by the Invention

In view of the fecal occult blood test technique, the problem of poor storage stability of a component in a collected feces sample has been pointed out. Moreover, when the amount of feces collected in feces sampling containers is small, the deactivation rate of hemoglobin is high and the storage stability, especially the storage stability at high temperatures, is poor. Objects of the present invention are to provide a feces sampling container to increase a storage stability of a component, such as hemoglobin, in a feces sample and to measure the component in a feces sample with a small amount of feces collected, a method for measuring a component in a feces sample, a method for stabilizing a component in a feces sample and a method for storing a feces sample.

Means to Solve the Object

The present inventors have diligently studied to achieve the aforementioned objects and obtained the findings that a component in a feces sample is stabilized by contacting a collected feces sample with a desiccant to dry the feces sample and storing the feces sample in a dried state in the desiccant, to complete the present invention.

Accordingly, the present invention relates to the following (1) to (19).

(1) A feces sampling container comprising:
a container body, and
a feces sampling stick having a gripping part on one side and a stick part on the other side, the stick part having a feces sampling part in the vicinity of the tip thereof;
wherein the container body comprises: an opening part through which the feces sampling part of the feces sampling stick is inserted, and a feces container chamber in which a desiccant is enclosed therein,
wherein the feces sample held by the feces sampling part is dried by a contact of the feces sampling part, which is inserted through the opening part and holding the feces sample, with the desiccant, and the feces sample in a dried state is stored in the desiccant.
(2) The feces sampling container according to (1), wherein the opening part comprises a leveling hole for removing excess feces.
(3) The feces sampling container according to (1) or (2), wherein the feces container chamber is formed with a fitting body fitted in the container body.
(4) The feces sampling container according to (3), wherein the fitting body is comprised of an upper fitting block and a lower fitting block.
(5) The feces sampling container according to any one of (1) to (4), wherein a bottom of the container body comprises a pierce part for introducing an aqueous medium for dissolving a component in the feces sample.
(6) The feces sampling container according to (3) or (4), wherein the fitting body comprises a pierce part for introducing an aqueous medium for dissolving a component in the feces sample in a top part thereof.
(7) The feces sampling container according to any one of (1) to (6), wherein the desiccant is a physical desiccant.
(8) The feces sampling container according to (7), wherein the physical desiccant is silica gel or aluminum oxide.
(9) A method for measuring a component in a feces sample, comprising: contacting a collected feces sample with a desiccant to dry the feces sample; storing the feces sample in a dried state in the desiccant; adding an aqueous medium to the desiccant, in which the feces sample in the dried state is stored, to dissolve the component in the feces sample in the aqueous medium; and measuring the component in the feces sample dissolved in the aqueous medium.
(10) The method for measurement according to (9), wherein the desiccant is a physical desiccant.
(11) The method for measurement according to (10), wherein the physical desiccant is silica gel or aluminum oxide.

(12) The method for measurement according to any one of (9) to (11), wherein the component in the feces sample is hemoglobin.
(13) A method for stabilizing a component in a feces sample, comprising contacting a collected feces sample with a desiccant to dry the feces sample; and storing the feces sample in a dried state in the desiccant.
(14) The method for stabilization according to (13), wherein the desiccant is a physical desiccant.
(15) The method for stabilization according to (14), wherein the physical desiccant is silica gel or aluminum oxide.
(16) The method for stabilization according to any one of (13) to (15), wherein the component in the feces sample is hemoglobin.
(17) A method for storing a feces sample, comprising contacting a collected feces sample with a desiccant to dry the feces sample; and storing the feces sample in a dried state in the desiccant.
(18) The method for storing according to (17), wherein the desiccant is a physical desiccant.
(19) The method for storing according to (18), wherein the physical desiccant is silica gel or aluminum oxide.

Effects of the Invention

The present invention provides a feces sampling container to increase a storage stability of a component, such as hemoglobin, in a feces sample and to measure a component in a feces sample with a small amount of feces collected; a method for measuring a component in a feces sample; a method for stabilizing a component in a feces sample; and a method for storing a feces sample. According to the present invention, a component in a feces sample is stabilized to afford a storage of a feces sample for a long period and a transportation of a feces sample in a dried state, such as that in mailing medical examination. According to the present invention, a component in a feces sample is stabilized to give an accurate measurement of a component in a feces sample.

BRIEF DESCRIPTION OF DRAWINGS

FIG. 1 is a schematic front view of a feces sampling container and a feces sampling stick according to the present invention.
FIG. 2 is a schematic view illustrating the contact between a feces sample and a desiccant (silica gel).
FIG. 3 illustrates one embodiment of use of the feces sampling container according to the present invention, illustrating a step of measuring a component in a feces sample by using the feces sampling container according to the present invention.
FIG. 4(a) is a perspective view of a feces sampling container comprising a pierce part in a top part of a fitting body and a hollow part through which an injection nozzle and an aspiration nozzle are inserted, in a gripping part.
FIG. 4(b) is a perspective view of a feces sampling container comprising a pierce part in a top part of a fitting body and no hollow part, through which an injection nozzle and an aspiration nozzle are inserted, in a gripping part.
FIG. 5 is a perspective view of a feces sampling container according to another aspect of the present invention, comprising pierce parts in both of a top face of a gripping part of a feces sampling stick and a top part of a fitting body.
FIG. 6 illustrates one embodiment of use of a feces sampling container according to another aspect of the present invention and the step of measuring a component in a feces sample by using the feces sampling container according to the present invention.
FIG. 7 illustrates a result of a hemoglobin stability test in pseudo-feces with silica gel.
FIG. 8 illustrates a result of a hemoglobin stability test in pseudo-feces using the feces sampling container according to the present invention.
FIG. 9 illustrates a result of a hemoglobin stability test in real feces with silica gel.
FIG. 10 illustrates a result of a hemoglobin stability test in pseudo-feces with aluminum oxide.

Figure 4A:
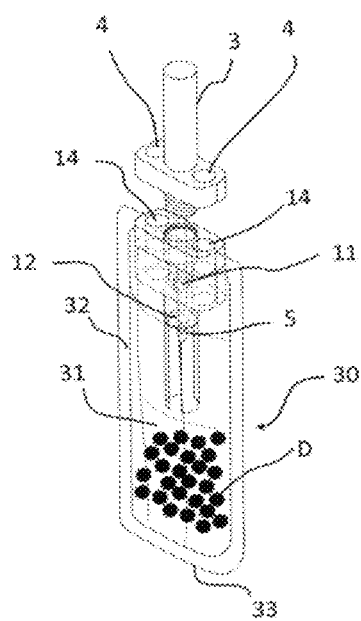
FIGS. 4(a) and 4(b) are a pair of perspective views of a feces sampling container according to one aspect of the present invention.

MODE OF CARRYING OUT THE INVENTION (1) Feces Sampling Container

The feces sampling container according to the invention comprises a container body, and a feces sampling stick having a gripping part on one side and a stick part on the other side, the stick part having a feces sampling part in the vicinity of the tip thereof, wherein the container body comprises: an opening part through which the feces sampling part of the feces sampling stick is inserted, and a feces container chamber in which a desiccant is enclosed therein, wherein the feces sample held by the feces sampling part is dried by a contact of the feces sampling part, which is inserted through the opening part and holding the feces sample, with the desiccant, and the feces sample in a dried state is stored in the desiccant.

As to the feces sample in the present invention, there is no restriction as long as it is a feces sample that can be collected using the feces sampling container according to the present invention. Examples include a feces separated from feces waste originated from humans, animals, and like. Examples of the animals include a monkey, a gorilla, an orangutan, a panda, a dog, a cat, a horse, a pig, a sheep, a wild boar, a rabbit, a mouse, a squirrel, a hamster, a tiger, a lion, a parrot, a parakeet, and a dove.

The component in the feces sample in the present invention may be any component, as long as it is a component present in the feces sample, and examples include hemoglobin, transferrin, calprotectin, elastase-1, enteric bacteria, and a pinworm. Moreover, the measurement of the component in a feces sample includes quantitative analysis and semi-quantitative analysis as well as qualitative analysis and detection of the component.

As to the desiccant in the present invention, there is no restriction as long as it can dry a feces sample and hold a component in the feces sample stably by contacting the desiccant with the feces sample, and examples include a physical desiccant that adsorbs water physically and a chemical desiccant using a chemical reaction or a property specific to a chemical substance such as the deliquescence, and a physical desiccant is preferred in that it does not change a component in the feces sample. Examples of the physical desiccant include a desiccant having a porous surface prone to adsorb water molecules. Specific examples include a water absorbent polymer such as silica gel, molecular sieve, allophane (a clay mineraloid made of amorphous or poorly crystalline hydrous aluminium silicate), aluminum oxide, zeolite, bentonite, clay, diatomaceous earth, titania and sodium polyacrylate, and silica gel and aluminum oxide are preferred. The chemical desiccant includes calcium oxide.

The physical desiccant is preferably used in a powder form held in a dried state, for example, an unpacked powder form held in a dried state form. Use of a physical desiccant in a powder form allows rapid contact with the feces sample, and upon the contact the feces sample can be dried rapidly.

In the present invention, "storing the feces sample in a dried state in a desiccant" means that "due to the contact between a feces sample and a desiccant, water in the feces sample is absorbed by the desiccant and the feces sample in a state where water has been absorbed, that is, a dried state is detached (released) from a feces sampling part of the feces sampling stick and held in the desiccant".

The feces sampling container according to the present invention comprises a container body and a feces sampling stick. The feces sampling stick has a gripping part on one side and a stick part on the other side, the stick part having a feces sampling part in the vicinity of the tip thereof. The container body comprises a feces container chamber. The feces container chamber may be made integrally with the container body, and it is preferable, in terms of easiness of producing, that it is formed with a fitting body fitted in the container body. When a fitting body is used, the container body has, on one side thereof, an opening part for fitting the fitting body therein and a bottom on the other side and a feces container chamber in which the desiccant is contained is formed in the space between a lower part of the container body (a part on the other side of the opening part of the container body) and the bottom of the fitting body. The fitting body has preferably a tubular guide part in which the stick part of the feces sampling stick can be inserted, a first leveling hole provided in the tubular guide part for removing excess feces, and a second leveling hole provided below the first leveling hole for further removing excess feces.

The gripping part provided on one side of the feces sampling stick has preferably a shape that allows the gripping part to enclose a desiccant, such as a shape that functions as a cap member of the feces sampling container, to prevent the moisture absorption of the desiccant in the feces container chamber (desiccant storage chamber), before feces collection operation and to prevent the feces sample in a dried state after the contact of the feces with the desiccant as well as the desiccant to spread outside, after feces collection operation. In order to impart the airtight function to the feces sampling stick having the gripping part as a cap member, it is possible to provide a screw part at the base end of the stick part of the feces sampling stick and install the feces sampling stick in an airtight condition by screwing and inserting the feces sampling stick in the inner peripheral surface of the opening part of the container body or to configure the base end of the stick part of the feces sampling stick to be insertable to the inner peripheral surface of the opening part of the container body in tight contact, and it is more preferable to provide a screw part at the base end of the stick part of the feces sampling stick.

The structure of the feces sampling part in the vicinity of the tip of the stick part of the feces sampling stick may be determined in view of a balance between the securement of quantitativity and the adhesion of the desiccant, and examples of the structure include one or more shapes of a concave part, a through-hole, and a trench part (an annular trench, an elongated trench, a helical trench, a diagonal-line trench, a V-shaped trench). As to the length of the stick part of the feces sampling stick, it is preferable that the feces sampling part in the vicinity of the tip of the stick part has a length that allows passing through the opening part of the container body, in particular, a length that allows passing through the opening part comprising a leveling hole for removing excess feces, and has a length that allows projecting into the feces container chamber in which the desiccant is contained. Examples of the material of the feces sampling stick include low-density polyethylene and ABS resin.

The container body may be a bottomed tubular container with a rectangular, oblong or rounded cross-section or a tube container with a sealed bottom part having, on one side thereof, an opening part in which the fitting body fits and a bottom part on the other side, and the trunk part (band part) of these containers, in particular, the tube container of a flexible material is preferred. Examples of the flexible material include a flexible resin such as polypropylene, polyethylene, polyester, polyvinyl chloride, and a laminated product of such a flexible resin.

In case the container body is a bottomed tubular container, the bottom of the container body is preferably a concave bottom comprising a pierce part for introducing an aqueous medium for dissolving a component in the feces sample, particularly preferably a tapered concave bottom that tapers towards the bottom (see FIG. 1). By making the bottom of the container body in a tapered concave shape that tapers towards the bottom, the tip of the nozzle for introducing an aqueous medium for dissolving a component in a feces sample into the feces container chamber can be certainly guided to a pierce part. The concave bottom comprising the pierce part preferably has a strength or structure that can be pierced by the tip of the nozzle.

Figure 4B:
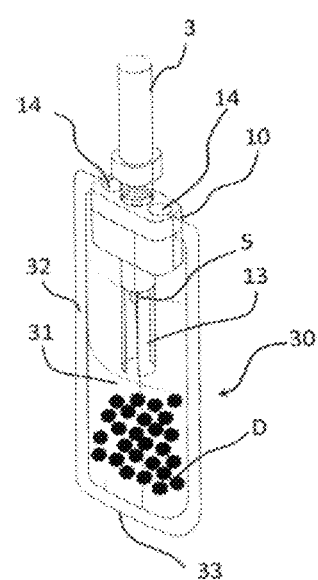

In case the container body is a tube container with a sealed bottom part, a structure comprising a pierce part in a top part of the fitting body to form a shoulder part of the tube container is preferred (see FIGS. 4(*a*) and 4(*b*)). In case the fitting body comprises an upper fitting block and a lower fitting block, a structure comprising a pierce part for introducing an aqueous medium for dissolving a component in the feces sample in a top part of the upper fitting block is preferable. The fitting body comprising a pierce part in the top part thereof preferably has a strength or structure that can be pierced by the tip of the nozzle for introducing an aqueous medium for dissolving a component in a feces sample into the feces container chamber. Moreover, in case the container body is a tube container, it may have a structure comprising a pierce part in the top face of a gripping part of the feces sampling stick for introducing an aqueous medium for dissolving a component in the feces sample (see FIG. 5). In this case, it is preferred to provide a pierce part also on a top part of a fitting body that is directly connected with the top face of the gripping part of the feces sampling stick. The gripping part comprising a pierce part in the top face thereof preferably has a strength or structure that can be pierced by the tip of the nozzle for introducing an aqueous medium for dissolving a component in a feces sample into the feces container chamber.

Moreover, the nozzle may be used as an aspiration nozzle of the aqueous medium in which a component in the feces sample is dissolved, and an aspiration nozzle far the aqueous medium in which a component in the feces sample is dissolved may be provided separately, and in this case, a filter may be provided on the nozzle tip.

The feces container chamber formed between a lower part of the container body and the lower side of the fitting body contains the aforementioned desiccant. Examples of the desiccant include the aforementioned desiccants. Moreover, the material of the container body is preferably a plastic through which the inside can be seen from the outside, and preferable examples include a flexible resin such as polypropylene, polyethylene, polyester and polyvinyl chloride, and a laminated product of such a flexible resin.

Examples of the aqueous medium for dissolving a component in a feces sample in the present invention include an aqueous medium such as deionized water, distilled water, and a buffer solution, and a buffer solution is preferred. Examples of the buffer solution include a phosphate buffer, a carbonate buffer, an ammonia buffer, an acetate buffer, a lactate buffer, a citrate buffer, a tartrate buffer, a borate buffer, a glycine buffer, Tris buffer, and a Good's buffer. Examples of a buffer used for the Good's buffer include 2-morpholinoethanesulfonic acid (MES), piperazine-N,N'-bis(2-ethanesulfonic acid) (PIPES), N-(2-acetamido)-2-aminoethanesulfonic acid (ACES), N,N-bis(2-hydroxyethyl)-2-aminoethanesulfonic acid (BES), bis(2-hydroxyethyl)imino-tris(hydroxymethyl)methane (Bis-Tris), 3-[N,N-bis(2-hydroxyethyl)amino]-2-hydroxypropanesulfonic acid (DIPSO), 3-[4-(2-hydroxyethyl)-1-piperazinyl] propanesulfonic acid [(H) EPPS], 2-[4-(2-hydroxyethyl)-1-piperazinyl] ethanesulfonic acid (HEPES), 3-[4-(2-hydroxyethyl)-1-piperazinyl]-2-hydroxypropanesulfonic acid (HEPPSO), 3-(morpholino)propanesulfonic acid (MOPS), 3-(morpholino)-2-hydroxypropanesulfonic acid (MOPSO), piperazine-N,N'-bis (2-hydroxypropanesulfonic acid) (POPSO), N-[tris(hydroxymethyl)methyl]-2-hydroxy-3-aminopropanesulfonic acid (TAPSO), N-[tris(hydroxymethyl)methyl]-2-aminoethanesulfonic acid (TES), N-(2-acetamido)iminodiacetic acid (ADA), N,N-bis(2-hydroxyethyl) glycine (Bicine), N-[tris(hydroxymethyl)methyl]glycine (Tricine), N-tris(hydroxymethyl)methyl-3-aminopropanesulfonic acid (TAPS), N-cyclohexyl-2-aminoethanesulfonic acid (CHES), N-cyclohexyl-3-aminopropanesulfonic acid (CAPS), N-cyclohexyl-3-amino-2-hydroxypropanesulfonic acid (CAPSO).

From the feces sample collected by the feces sampling stick, excess feces is removed through both of a first leveling hole and a second leveling hole in the fitting body described later. Subsequently, the feces sample after the removal of excess feces is directly contacted with a desiccant contained in the feces container chamber to be dried, and the feces sample in a dried state is stored in the desiccant. As to the method for directly contacting the feces sample after the removal of excess feces with the desiccant contained in the feces container chamber, there is no restriction as long as it is a method for directly contacting a feces sample with a desiccant, and examples include a method involving inserting a feces sampling stick in a desiccant and a method involving vibrating or shaking a feces sampling container to directly contact a feces sample with a desiccant. Moreover, in case the container body is a tube container, the tube container preferably has flexibility, and the tube container having the property allows direct contact between the feces sample and the desiccant in the feces container chamber by applying pressure to the container body. In particular, applying pressure to the trunk part (barrel part) of the container body is preferable for contacting the feces sample with the desiccant each other efficiently. By directly contacting the feces sample and the desiccant with each other, water in the feces sample is absorbed by the desiccant to produce a feces sample in a dried state, and the feces sample in a dried state is detached and falls off from the feces sampling part and stored in the desiccant. In case a component in the feces sample is subsequently measured, the measurement can be performed by adding an aqueous medium to the desiccant in which the feces sample in the dried state is stored to dissolve the component in the feces sample in the aqueous medium and analyzing the component in the feces sample dissolved in the aqueous medium on an analysis system. As to the analysis system, there is no restriction as long as it is a system that can analyze the component in the feces sample dissolved in the aqueous medium, and examples thereof in case the component in the feces sample is hemoglobin include a hemoglobin analyzer. Examples of the hemoglobin analyzer include a fully automated fecal hemoglobin analyzer such as HM-JACK or HM-JACKarc (both manufactured by Kyowa Medex Co., Ltd.).

The fitting body to be fitted to the inner part of the container body preferably has a tubular guide part capable of liquid-tightly shielding the inside of the container body into an upper part of the feces container chamber and a lower part of the faces container chamber and permitting insertion of the stick part of the feces sampling stick; a first leveling hole provided in the tubular guide part for removing excess feces; and a second leveling hole provided below the first leveling hole for further removing excess feces. Example of the fitting body include a fitting body composed of a single fitting block provided with the first leveling hole and the second leveling hole on the tubular guide part; and a fitting body composed of a plurality of fitting blocks, for example, a fitting body composed of an upper fitting block provided with the first leveling hole on the tubular guide part and a lower fitting block provided with the second leveling hole (see the aforementioned patent document 1). In case the fitting body is composed of a single fitting block, a fixing member for fixing the vicinity of the lower end of the tubular guide part to the container body is preferably formed integrally with the tubular guide part. In case a fitting body is composed of an upper fitting block and a lower fitting block and the upper fitting block has a first leveling hole of the tubular guide part, the lower fitting block is preferably provided with a hold part for the lower portion of the tubular guide part in the upper fitting block. The fitting body described above may be fixed airtight by fitting it in the container body or fixed airtight by using a fitting body support separately.

The second leveling hole provided in the fitting body preferably has an opening area (hole diameter) smaller than the opening area (hole diameter) of the first leveling hole for thereby removing excess feces attached to the feces sampling part of the feces sampling stick through the first leveling hole and collecting feces quantitatively by further removing excess feces through the second leveling hole. In addition, the opening area (hole diameter) of the first leveling hole and that of the second leveling hole of the fitting body are preferably smaller than the cross-sectional area (stick diameter) of the feces sampling part of the feces sampling stick. By making the opening area (hole diameter) of the first leveling hole of the fitting body smaller than the cross-sectional area (stick diameter) of the feces sampling part of the feces sampling stick, excess feces attached to the feces sampling part of the feces sampling stick can be removed efficiently through the first leveling hole. By making the opening area (hole diameter) of the second leveling hole of the fitting body smaller than the cross-sectional area (stick diameter) of the feces sampling part of the feces sampling stick and the opening area (hole diameter) of the first leveling hole, quantitative collection of feces through the second leveling hole can be achieved. Furthermore, in order to prevent leakage of the desiccant, the second leveling hole may be provided with a thin-film sealing film, or the second leveling hole may have a structure in which the second leveling hole is closed when the stick part of the feces sampling stick is pulled out.

In the case where the feces sampling stick comprises a male screw part at the base end of the stick part thereof for screwing the feces sampling stick while inserting the feces sampling stick into a female screw provided on the top part of the fitting body, excess feces attached to the feces sampling part of the feces sampling stick to slide down on the downward helix slope of the helical structure due to a friction pressure when the feces sample container of the invention is equipped with a part having a different levels in which the opening area of the first leveling hole is smaller than the internal cross-section area of the tubular guide part adjacent to the upper end of the first leveling hole, with the excess feces being compressed by the helical structure protruding to the inner surface side of the tubular guide part adjacent to the upper end of the first leveling hole of the fitting body. The feces are accumulated and stored in the non-different level portion of the protruding helical structure, this non-differential level portion of the protruding helical structure placed at a predetermined position in advance is formed as a feces collection-detecting domain. It is particularly preferred to form the helical structure so that the helix rotation angle of the feces sampling stick to be inserted while screwed be set within a range of from 200 to 260 degrees, because the excess feces attached to the feces sampling part of the feces sampling stick slides down on the downward helix slope of the helical structure by a friction pressure with the excess feces being compressed by the helical structure protruding to the inner surface side of the tubular guide part, and then is accumulated and stored in the part non-different level portion of the protruding helical structure (from 160 to 100 degrees).

The tubular guide part preferably has a gradual reverse tapered structure, which terminates at the part having different levels at the upper end of the first leveling hole. Such a structure enables a smooth introduction of the feces sampling part of the feces sampling stick to the first leveling hole. The reverse tapered structure extending from the first leveling hole to the upper part adjacent to the second leveling hole or extending from the first leveling hole to the second leveling hole is preferred for smooth guide of the feces sampling part of the feces sampling stick from the first leveling hole to the second leveling hole. The portion of the tubular guide part downward from the first leveling hole has usually a tubular shape having the same diameter.

As the material for forming the fitting body, soft flexible resins such as polyethylene, polypropylene, polyester, soft polyvinyl chloride, and olefin elastomer can be commonly used in consideration of the liquid-tight sealing property, attachment to the container body by insertion, and easy insertion of the feces sampling stick into the first and second leveling holes.

It is preferred to attach a label to the outside of the feces sampling container so as to extend it in a J shape from the gripping part to one of the side surfaces, the bottom, and the other side surface of the container body. The label may be provided with a cutout window for confirming collection of feces so that the collected-feces detecting domain can be seen directly. This label can be used not only as a label for identifying the name and sex of the test subject, feces collection date, and the like but is also useful for protection and contamination prevention of the pierce part at the bottom of the container body when the container body is a bottomed tubular container.

(2) Method for Measuring a Component in a Feces Sample

The method for measuring a component in a feces sample according to the present invention is a method comprising contacting a collected feces sample with a desiccant to dry the feces sample; storing the feces sample in a dried state in the desiccant; adding an aqueous medium to the desiccant in which the feces sample in the dried state is stored to dissolve the component in the feces sample in the aqueous medium; and detecting or measuring the component in the feces sample dissolved in the aqueous medium. In the method for measurement according to the present invention, the feces sample in a dried state may be obtained using the feces sampling container according to the present invention, or the like. Examples of the feces sample used in the method for measurement according to the present invention include the aforementioned feces sample. Examples of the component in the feces sample in the method for measurement according to the present invention include the aforementioned components in feces sample. Examples of the desiccant and the aqueous medium in the method for measurement according to the present invention include the aforementioned desiccant and aqueous medium, respectively.

Examples of the method for measurement according to the present invention include a method comprising the following steps.

[1] a step of obtaining a feces sample with a feces sampling part of a feces sampling stick;

[2] a step of directly contacting the feces sample obtained in the step [1] with a desiccant to dry the feces sample;

[3] a step of storing the feces sample in a dried state, detached from the feces sampling part of the feces sampling stick obtained in the step [2], in the desiccant;

[4] a step of adding an aqueous medium to the desiccant in the step [3] to dissolve a component in the feces sample in the aqueous medium and to obtain an aqueous solution containing the component;

[5] a step of measuring the component in the aqueous solution obtained in the step [4];

[6] a step of determining the concentration of the component in the aqueous solution based on a standard curve prepared in advance representing the relation between the concentration of the component and an amount of information derived from the component, and the measurement obtained in the step [5];

[7] a step of determining the content of the component in the sample based on the concentration determined in the step [6] and the volume of the aqueous medium added in the step [4].

The method used for the measurement of the component in the feces sample in the step [5] may be any method, as long as it is a method that can accurately measure the component in the feces sample, and a method known to those skilled in the art may be used. In case the component in the feces sample is hemoglobin, then the measurement may be performed using, for example, commercially available products such as "EXTEL HEMO-AUTO" (manufactured by Kyowa Medex Co., Ltd.) and "Nescoat Hemo-Plus" (manufactured by Alfresa Pharma Corporation). In case the component in the feces sample is transferrin, then the measurement may be performed using, for example, commercially available products such as "Nescoat transferrin Plus" (manufactured by Alfresa Pharma Corporation). The measurement of the component in the aqueous solution obtained in the step [4] may be performed using a fully automated fecal component analyzer such as the aforementioned fully automated fecal hemoglobin analyzers.

As one embodiment of the use of the feces sampling container according to the present invention, a method for measuring a component in a feces sample using the feces sampling container according to the present invention will be described with reference to FIGS. 1 to 6. A feces sampling stick 2 is removed from a feces sampling container 1 (see FIG. 1) and feces is collected by sticking a feces sampling part 5 in a feces or rubbing the surface of the feces with a feces sampling part 5, holding a gripping part 3 of the feces sampling stick 2 with hand. Then, a stick part 7 of the feces sampling stick 2 is inserted in a bottomed tubular container body 20 in an upright state via a tubular guide part 13 of a fitting body 10, and the gripping part 3 of the feces sampling stick 2 is pushed down and rotated to screw a male screw provided on a stick part base end 6 of the feces sampling stick 2 with a female screw provided on a top part of a fitting body and to seal the container body 20. In addition, the feces sampling part 5 of the feces sampling stick 2 is inserted through a first leveling hole 11 and a second leveling hole 12 to remove excess feces attached to the feces sampling stick 2. The amount of the feces obtained after removing excess feces is usually 1 to 10 mg. Then, the feces sampling container 1 is shaken well to directly contact a feces sample B with a desiccant D. By the contact of the feces sample B with the desiccant D, water in the feces sample is absorbed by the desiccant D, and a feces sample $B_D$ in a state where water has been absorbed, that is to say, in a dried state is detached from the feces sampling part and falls and is held in the desiccant (see FIG. 2). Test subjects can send a feces sampling container 1 in this state to an inspection facility such as a hospital, an inspection institute, or the like by mail or another way. In the inspection facility such as a hospital, an inspection institute, or the like, a tip of an injection nozzle for an aqueous medium for dissolving a component in a feces sample (liquid for suspending feces) is made to penetrate a pierce part 14 in the bottom of the container body with the feces sampling container 1 in an upside-down state, and the aforementioned aqueous medium is added to the feces sample $B_D$ in a dried state. A component in the feces sample is dissolved in the aqueous medium to prepare an aqueous solution of the component and the prepared aqueous solution of the component is aspirated with the aspiration nozzle. Using the aspirated aqueous solution as a sample, the component in the aqueous solution can be measured on an analysis system (see FIG. 3). On the analysis system, the component is measured by a method such as the absorptiometry, the luminescence method, the fluorescence method, the turbidimetry, or the like. The aspiration nozzle to be used may be the same nozzle as the aforementioned injection nozzle.

Moreover, a feces sampling container comprising a pierce part 14 for introducing an aqueous medium for dissolving a component in a feces sample in a top part of a fitting body 10 and having a hollow part through which an injection nozzle and an aspiration nozzle are inserted in a gripping part of a feces sampling stick [see FIG. 4 (a)] and a feces sampling container comprising a pierce part 14 for introducing an aqueous medium for dissolving a component in a feces sample in a top part of a fitting body 10, and having no hollow part through which an injection nozzle and an aspiration nozzle are inserted in a gripping part of a feces sampling stick [see FIG. 4 (b)] may be used. Moreover, a feces sampling container comprising pierce parts 8, 14 for introducing an aqueous medium for dissolving a component in a feces sample in both of a top face 9 of a gripping part of a feces sampling stick and a top part of a fitting body 10 directly connected with the top face (see FIG. 5) may be used. A feces sampling stick 2 is removed from a feces sampling container 1 and feces is collected by sticking a feces sampling part 5 of the feces sampling stick 2 in a feces or rubbing the surface of the feces with a feces sampling part 5 of the feces sampling stick 2. Then, a stick part 7 of the feces sampling stick 2 is inserted in a container body 30 in an upright state via a tubular guide part 13 of a fitting body 10, and the gripping part 3 of the feces sampling stick 2 is pushed down and rotated to screw a male screw provided on a stick part base end 6 of the feces sampling stick 2 with a female screw provided on a top part of fitting body and to seal the container body 30. In addition, the feces sampling part 5 of the feces sampling stick 2 is inserted through both of a first leveling hole 11 and a second leveling hole 12 to remove excess feces attached to the feces sampling stick 2. The amount of the feces obtained after removing excess feces is usually 1 to 10 mg. Then, the feces sampling container 1 is shaken well to directly contact a feces sample B with a desiccant D. By the contact of the feces sample B with the desiccant D, water in the feces sample is absorbed by the desiccant, and a feces sample $B_D$ in a state where water has been absorbed, that is to say, in a dried state, is detached from the feces sampling part and falls and is held in the desiccant. Test subjects can send a feces sampling container in this state to an inspection facility such as a hospital, an inspection institute, or the like by mail or another way. In the inspection facility such as a hospital, an inspection institute or the like, a tip of an injection nozzle for an aqueous medium for dissolving a component in a feces sample (liquid for suspending feces) is penetrated into the pierce part 14 in the top part of the fitting body, or both of the pierce part 8 in the top face 9 of the gripping part of the feces sampling stick and the pierce part 14 of the top part of the fitting body, with the feces sampling container in an upright state without turning it into an upside-down state, and the aforementioned aqueous medium is added to the feces sample $B_D$ in a dried state. A component in the feces sample is dissolved in the aqueous medium to prepare an aqueous solution of the component. At this time, in case the container body of the feces sampling container is a tube container, then the component can be dissolved in the aqueous medium efficiently by applying pressure to a trunk part 32 of the container body 30. The pressure may be applied to the trunk part 32 of the container body 30 on one side or both sides of the container body. In case the pressure is applied on both sides of the container body 30, the pressure may be applied to the right and left trunk parts 32 alternately or the pressure may be applied to the right and left trunk parts 32 simultaneously. And the prepared aqueous solution of the component is aspirated by an aspiration nozzle. Using the aspirated aqueous solution as a sample, the component in the aqueous solution can be measured on an analysis system such as a fully automated fecal component analyzer (see FIG. 6). On the analysis system, the component is measured by a method such as the absorptiometry, the luminescence method, the fluorescence method, the turbidimetry, or the like. The aspiration nozzle to be used may be the same nozzle as the aforementioned injection nozzle.

(3) Method for Stabilizing Component in Feces Sample

The method for stabilizing a component in a feces sample according to the present invention comprises contacting a collected feces sample with a desiccant to dry the feces sample; and storing the feces sample in a dried state in the desiccant. Examples of the feces sample, the component in a feces sample, and the aqueous medium in the method of stabilization according to the present invention include the aforementioned feces sample, the aforementioned component in a feces sample, and the aforementioned aqueous medium, respectively. The stabilization of the component in a feces sample may be evaluated using a pseudo-feces instead of a real feces. The pseudo-feces is an artificial feces prepared by adding a component in feces such as hemoglobin to a matrix having physical properties that resemble those of feces (stool) and is used for quality control of the fecal occult blood test, etc. Examples of the matrix include roasted soybean flour, mashed potato, buckwheat flour, refined rice flour, starch powder, ground sesame seeds, cornstarch, and inorganic powder disclosed in Japanese unexamined Patent Application Publication No. 11-242027 and Japanese unexamined Patent Application Publication No. 2003-185654. Moreover, the pseudo-feces may be prepared using a commercially available control sample. Examples of the commercially available control sample include the control sample for an immunological fecal occult blood measurement reagent, Haemo control (manufactured by Kyokuto Pharmaceutical Industrial Co., Ltd.).

In the present invention, the term "stable" means that the concentration or activity of the component in a feces sample is maintained even after storage of the feces sample for a long time. More specifically, it means that in case a pseudo-feces is used as a feces sample, the feces sample is stored at 40° C. for 6 days or at 50° C. for 5 days and the concentration or activity of the component after the storage at 40° C. for 6 days or at 50° C. for 5 days is 40% or more, and preferably 50% or more of the concentration or activity of the component just before the storage of the feces sample at 40° C. or 50° C. In addition, it means that in case a real feces is used as a feces sample, the feces sample is stored at 40° C. for 3 days and the concentration or activity of the component after the storage at 40° C. for 3 days is 30% or more, and preferably 40% or more of the concentration or activity of the component just before the storage of the feces sample at 40° C. The concentration or activity of the component in a feces sample can be measured, for example, by the aforementioned method.

The stabilization of the component in a feces sample can be evaluated, for example, by the following method. A certain amount of the feces sample is dissolved in a liquid for suspending feces in a commercially available feces sampling container to prepare a sample$_{(control:\ for\ 0\ days)}$ for evaluation of feces stability. This sample$_{(control:\ for\ 0\ days)}$ for evaluation of feces stability is stored at 40° C. or 50° C. for a certain time to prepare a sample$_{(control:\ after\ storage)}$ for evaluation of feces stability. Using the sample$_{(control:\ for\ 0\ days)}$ for evaluation of feces stability and the sample$_{(control:\ after\ storage)}$ for evaluation of feces stability prepared, the component concentrations $C_{(control:\ for\ 0\ days)}$ and $C_{(control:\ after\ storage)}$ in each of the samples for evaluation of feces stability are determined by the aforementioned method for measuring a component (for example, hemoglobin) in a feces sample. From the component concentration $C_{(control:\ for\ 0\ days)}$ and the component concentration $C_{(control:\ after\ storage)}$ determined, the percent remaining of the component in the control sample is calculated by the following formula (I).

$$\text{Percent remaining (\%)} = C_{(control:\ after\ storage)} / C_{(control:\ for\ 0\ days)} \times 100 \quad (I)$$

A certain amount of the feces sample is added to a container filled with a certain amount of a desiccant, and the feces sample is mixed with the desiccant in the container to prepare a dried feces sample$_{(the\ present\ invention:\ for\ 0\ days)}$. This dried feces sample$_{(the\ present\ invention:\ for\ 0\ days)}$ is stored at 40° C. or 50° C. for a certain time to prepare a dried feces sample$_{(the\ present\ invention:\ after\ storage)}$. To each of the dried feces sample$_{(the\ present\ invention:\ for\ 0\ days)}$ and the dried feces sample$_{(the\ present\ invention:\ after\ storage)}$ prepared, a certain amount of an aqueous medium is added, and the supernatants obtained by leaving the mixtures for a certain time are collected as a sample$_{(the\ present\ invention:\ for\ 0\ days)}$ for evaluation of feces stability and a sample$_{(the\ present\ invention:\ after\ storage)}$ for evaluation of feces stability. By the aforementioned method for measuring a component (for example, hemoglobin) in a feces sample, the component concentrations $C_{(the\ present\ invention:\ for\ 0\ days)}$ and $C_{(the\ present\ invention:\ after\ storage)}$ in each of the samples for evaluation of feces stability are determined. From the component concentration $C_{(the\ present\ invention:\ for\ 0\ days)}$ and the component concentration $C_{(the\ present\ invention:\ after\ storage)}$ determined, the percent remaining of the component in the dried feces sample is calculated by the following formula (II).

$$\text{Percent remaining (\%)} = C_{(the\ present\ invention:\ after\ storage)} / C_{(the\ present\ invention:\ for\ 0\ days)} \times 100 \quad (II)$$

For both of the percent remaining of the component in the control sample calculated by formula (I) above and the percent remaining of the component in the dried feces sample calculated by formula (II) above, it is evaluated that the closer to 100% the value is, the more stably the component has been held. In case the percent remaining of the component in the dried feces sample is higher than the percent remaining of the component in the control sample, the component in the feces sample can be evaluated to be stabilized.

In the method of stabilization according to the present invention, a surfactant, a preservative, a protein, a sugar, or the like may be present together with a desiccant. Examples of the surfactant include a non-ionic surfactant, a cationic surfactant, an anionic surfactant, and an amphoteric surfactant. Examples of the preservative include an azide and a chelating agent, and examples of the azide include sodium azide. Examples of the chelating agent include ethylenediaminetetraacetic acid (EDTA) or a salt thereof, and examples of the salt include a sodium salt and a potassium salt. Examples of the protein include albumin, and examples of the albumin include bovine serum albumin (BSA). Examples of the sugar include trehalose and sucrose.

(4) Method for Storing Feces Sample

The method for storing a feces sample according to the present invention comprises contacting a collected feces sample with a desiccant to dry the feces sample; and storing the feces sample in a dried state in the desiccant. Examples of the feces sample in the method for storing according to the present invention include the aforementioned feces sample. As to the duration of storage in the method for storing a feces sample according to the present invention, there is no restriction as long as it is a duration for which the feces sample is stored stably, and it is usually 30 minutes to 30 days and preferably 1 to 5 days. Moreover, as to the storage temperature in the method for storing a feces sample according to the present invention, there is no restriction as long as it is a temperature at which the feces sample is stored stably, and it is usually −80 to 60° C. and preferably 0 to 50° C. In the method for storing a feces sample according to the present invention, a surfactant, a preservative, a protein, a sugar, or the like may coexist with a desiccant. Examples of the surfactant include a non-ionic surfactant, a cationic surfactant, an anionic surfactant, and an amphoteric surfactant. Examples of the preservative include an azide and a chelating agent, and examples of the azide include sodium azide. Examples of the chelating agent include ethylenediaminetetraacetic acid (EDTA) or a salt thereof, and examples of the salt include a sodium salt and a potassium salt. Examples of the protein include albumin, and examples of the albumin include bovine serum albumin (BSA). Examples of the sugar include trehalose and sucrose.

The present invention will be described referring to Examples in more detail, but these do not limit the technical scope of the present invention. In the Examples, instruments, reagents, and samples from the following manufacturers were used.

Instruments

Fully automated fecal human hemoglobin analyzer HM-JACKarc (manufactured by Kyowa Medex Co., Ltd.)

Incubator AS ONE SHAKING INCUBATOR SI-300 (manufactured by As One Corporation)

Reagents

EXTEL "HEMO-AUTO" HS L liquid (manufactured by Kyowa Medex Co., Ltd.)

EXTEL hemoglobin standard HS (manufactured by Kyowa Medex Co., Ltd.)

EXTEL HM control HS (manufactured by Kyowa Medex Co., Ltd.)

EXTEL "HEMO-AUTO" buffer solution (manufactured by Kyowa Medex Co., Ltd.)

HEMO-AUTO MC feces sampling container (manufactured by Kyowa Medex Co., Ltd.)

Liquid N for suspending feces (manufactured by Kyowa Medex Co., Ltd.) contained in HEMO-AUTO MC feces sampling container Silica gel (a desiccant for dried flower) (manufactured by Toyotakako Co., Ltd.)

Aluminum oxide (manufactured by Sigma-Aldrich)

EXAMPLES

Example 1

Stability of Hemoglobin in Pseudo-Feces (1)—Study with Container Filled with Silica Gel (1) Preparation of Pseudo-Feces Among three powder samples A to C and three solubilization liquids A to C enclosed in Haemo control (manufactured by Kyokuto Pharmaceutical Industrial Co., Ltd), a control sample for an immunological fecal occult blood measurement reagent, both of the powder sample B and the solubilization liquid B were used to prepare a pseudo-feces. Specifically, the solubilization liquid B (2 mL) is added to the powder sample (2 g), and the mixture was left at 25° C. for 30 minutes and stirred with a stirring stick attached to the control sample to prepare a pseudo-feces.

(2) Preparation of Container Filled with Silica Gel

A screw cap Spitz tube (10 mL, manufactured by Eiken Chemical Co., Ltd.) was filled with 1.4 g of silica gel to prepare a container filled with silica gel.

(3) Preparation of Pseudo-Feces Sample (3-1) Pseudo-Feces Sample for Control

The pseudo-feces prepared in above (1) was collected using a feces sampling stick, a component of HEMO-AUTO MC feces sampling container. The feces sampling stick holding the collected pseudo-feces was inserted in the main body of the HEMO-AUTO MC feces sampling container while being rotated and pushed down, and the pseudo-feces was dissolved in Liquid N for suspending feces in the HEMO-AUTO MC feces sampling container to prepare Pseudo-feces sample $1_{(control:\ for\ 0\ days)}$.

(3-2) Pseudo-Feces Sample According to the Present Invention

The pseudo-feces prepared in above (1) was collected using a feces sampling stick, a component of HEMO-AUTO MC feces sampling container. The collected pseudo-feces was directly inserted in a leveling hole of a lower fitting block (separator) [see Patent Document 1 stated above (40 in FIG. 9)], a component of the HEMO-AUTO MC feces sampling container, and excess pseudo-feces attached to the feces sampling stick was removed. Subsequently, a tip part (a part up to approximately 2 cm from the tip) of the feces sampling stick after excess pseudo-feces was removed was cut with a nipa and added to the screw cap Spitz tube of above (2). Then, the screw cap Spitz tube containing the tip part of the feces sampling stick holding the pseudo-feces was closed with the screw cap, and the screw cap Spitz tube was stirred sufficiently to mix the pseudo-feces with silica gel in the screw cap Spitz tube and to prepare Pseudo-feces sample $1_{(the\ present\ invention:\ for\ 0\ days)}$.

(4) Preparation of Sample for Evaluation of Storage Stability (4-1) Preparation of Control Sample for Evaluation of Storage Stability Pseudo-feces sample $1_{(control:\ for\ 0\ days)}$ prepared in above (3-1) was stored in an incubator at 50° C. for 24 hours to prepare Pseudo-feces sample $1_{(control:\ for\ 1\ day)}$. Similarly, Pseudo-feces sample $1_{(control:\ for\ 0\ days)}$ was stored in an incubator at 50° C. for 48 hours to prepare Pseudo-feces sample $1_{(control:\ for\ 2\ days)}$. Similarly, Pseudo-feces sample $1_{(control:\ for\ 0\ days)}$ was stored in an incubator at 50° C. for 72 hours to prepare Pseudo-feces sample $1_{(control:\ for\ 3\ days)}$. Similarly, Pseudo-feces sample $1_{(control:\ for\ 0\ days)}$ was stored in an incubator at 50° C. for 96 hours to prepare Pseudo-feces sample $1_{(control:\ for\ 4\ days)}$. Similarly, Pseudo-feces sample $1_{(control:\ for\ 0\ days)}$ was stored in an incubator at 50° C. for 120 hours to prepare Pseudo-feces sample $1_{(control:\ for\ 5\ days)}$. Each of prepared Pseudo-feces sample $1_{(control:\ for\ 0\ days)}$, Pseudo-feces sample $1_{(control:\ for\ 1\ day)}$, Pseudo-feces sample $1_{(control:\ for\ 2\ days)}$, Pseudo-feces sample $1_{(control:\ for\ 3\ days)}$, Pseudo-feces sample $1_{(control:\ for\ 4\ days)}$, and Pseudo-feces sample $1_{(control:\ for\ 5\ days)}$ was used as a control sample for evaluation of storage stability [sample $1_{(control:\ for\ 0\ days)}$ for evaluation of storage stability; Sample $1_{(control:\ for\ 1\ day)}$ for evaluation of storage stability; Sample $1_{(control:\ for\ 2\ days)}$ for evaluation of storage stability; Sample $1_{(control:\ for\ 3\ days)}$ for evaluation of storage stability; Sample $1_{(control:\ for\ 4\ days)}$ for evaluation of storage stability; Sample $1_{(control:\ for\ 5\ days)}$ for evaluation of storage stability], respectively.

(4-2) Preparation of Sample for Evaluation of Storage Stability According to the Present Invention Pseudo-feces sample $1_{(the\ present\ invention:\ for\ 0\ days)}$ prepared in above (3-2) was stored in an incubator at 50° C. for 24 hours to prepare Pseudo-feces sample $1_{(the\ present\ invention:\ for\ 1\ day)}$. Similarly, Pseudo-feces sample $1_{(the\ present\ invention:\ for\ 0\ days)}$ was stored in an incubator at 50° C. for 48 hours to prepare Pseudo-feces sample $1_{(the\ present\ invention:\ for\ 2\ days)}$. Similarly, Pseudo-feces sample $1_{(the\ present\ invention:\ for\ 0\ days)}$ was stored in an incubator at 50° C. for 72 hours to prepare Pseudo-feces sample $1_{(the\ present\ invention:\ for\ 3\ days)}$. Similarly, Pseudo-feces sample $1_{(the\ present\ invention:\ for\ 0\ days)}$ was stored in an incubator at 50° C. for 96 hours to prepare Pseudo-feces sample $1_{(the\ present\ invention:\ for\ 4\ days)}$. Similarly, Pseudo-feces sample $1_{(the\ present\ invention:\ for\ 0\ days)}$ was stored in an incubator at 50° C. for 120 hours to prepare Pseudo-feces sample $1_{(the\ present\ invention:\ for\ 5\ days)}$.

Liquid N for suspending feces (4 mL) contained in the HEMO-AUTO MC feces sampling container was added to each screw cap Spitz tube containing each prepared pseudo-feces sample according to the present invention. Subsequently, the screw cap Spitz tubes were closed with screw caps and each screw cap Spitz tube was stirred with a vortex mixer for 1 minute to mix silica gel holding the pseudo-feces with Liquid N for suspending feces in each screw cap Spitz tube. After stirring, each screw cap Spitz tube was left to stand, and the supernatant in each screw cap Spitz tube was collected as a sample for evaluation of storage stability according to the present invention [Sample $1_{(the\ present\ invention:\ for\ 0\ days)}$ for evaluation of storage stability; Sample $1_{(the\ present\ invention:\ for\ 1\ day)}$ for evaluation of storage stability; Sample $1_{(the\ present\ invention:\ for\ 2\ days)}$ for evaluation of storage stability; Sample $1_{(the\ present\ invention:\ for\ 3\ days)}$ for evaluation of storage stability; Sample $1_{(the\ present\ invention:\ for\ 4\ days)}$ for evaluation of storage stability; Sample $1_{(the\ present\ invention:\ for\ 5\ days)}$ for storage evaluation of stability].

(5) Measurement of Hemoglobin in Sample for Evaluation of Storage Stability (5-1) Measurement of Hemoglobin in Control Sample for Evaluation of Storage Stability Using EXTEL "HEMO-AUTO" HS L liquid and EXTEL "HEMO-AUTO" buffer solution, hemoglobin in the control samples for evaluation of storage stability prepared in above (4-1) were measured with HM-JACKarc.

(a) Preparation of Standard Curve

In accordance with a method described in a package insert of EXTEL "HEMO-AUTO" HS, a standard curve showing the relation between the hemoglobin concentration and the turbidity was prepared using EXTEL hemoglobin standard HS and EXTEL HM control HS.

(b) Determination of Hemoglobin Concentration in Control Sample for Evaluation of Storage Stability EXTEL "HEMO-AUTO" HS L liquid (90 μL) and EXTEL "HEMO-AUTO" buffer solution (190 μL) were added to a cup for exclusive use for HM-JACKarc, and Control Sample $1_{(control:\ for\ 0\ days)}$ (4 μL) for evaluation of storage stability prepared in (4-1) was then added to perform a reaction at 25° C. The turbidity 108 seconds after the addition of Control Sample $1_{(control:\ for\ 0\ days)}$ for evaluation of storage stability and the turbidity 306 seconds after the addition were measured, and the turbidity 108 seconds after the addition was subtracted from the turbidity 306 seconds after the addition. The obtained value was compared with the standard curve generated in (a), and the hemoglobin concentration in Control Sample $1_{(control:\ for\ 0\ days)}$ for evaluation of storage stability was determined.

As a control sample for evaluation of storage stability, each of Control Sample $1_{(control:\ for\ 1\ day)}$ for evaluation of storage stability; Control Sample $1_{(control:\ for\ 2\ days)}$ for evaluation of storage stability; Control Sample $1_{(control:\ for\ 3\ days)}$ for evaluation of storage stability; Control Sample $1_{(control:\ for\ 4\ days)}$ for evaluation of storage stability; and Control Sample $1_{(control:\ for\ 5\ days)}$ for evaluation of storage stability was used instead of Control Sample $1_{(control:\ for\ 0\ days)}$ for evaluation of storage stability to perform a similar measurement, and the hemoglobin concentration in each of the control samples for evaluation of storage stability was determined. The hemoglobin concentration in each of the control samples for evaluation of storage stability relative to the hemoglobin concentration in Control Sample $1_{(control:\ for\ 0\ days)}$ for evaluation of storage stability, defined to be 100 is illustrated in Table 1 and FIG. 7.

(5-2) Measurement of Hemoglobin in Sample for Evaluation of Storage Stability According to the Present Invention Except that a sample for evaluation of storage stability according to the present invention prepared in above (4-2), that is, each of Sample $1_{(the\ present\ invention:\ for\ 0\ days)}$ for evaluation of storage stability, Sample $1_{(the\ present\ invention:\ for\ 1\ day)}$ for evaluation of storage stability, Sample $_{(the\ present\ invention:\ for\ 2\ days)}$ for evaluation of storage stability, Sample $1_{(the\ present\ invention:\ for\ 3\ days)}$ for evaluation of storage stability, Sample $1_{(the\ present\ invention:\ for\ 4\ days)}$ for evaluation of storage stability, and Sample $1_{(the\ present\ invention:\ for\ 5\ days)}$ for evaluation of storage stability was used as a sample for evaluation of storage stability instead of a control sample for evaluation of storage stability, the hemoglobin concentration in each of the samples for evaluation of storage stability was determined by a method similar to that of (5-1). The hemoglobin concentration in each of the samples for evaluation of storage stability relative to the hemoglobin concentration in Sample $1_{(the\ present\ invention:\ for\ 0\ days)}$ for evaluation of storage stability, defined to be 100, is illustrated in Table 1 and FIG. 7.

TABLE 1

| Days of storage (Days) | Hemoglobin concentration in sample for evaluation of storage stability (%) | |
|---|---|---|
| | Present invention | Control |
| 0 | 100 | 100 |
| 1 | 95 | 14 |
| 2 | 84 | 10 |
| 3 | 98 | 6 |
| 4 | 102 | 9 |
| 5 | 104 | 9 |

As apparent from Table 1 and FIG. 7, while the hemoglobin concentration in the control sample for evaluation of storage stability prepared by dissolving a pseudo-feces in Liquid N for suspending feces was decreased to 14% after storage at 50° C. only for 1 day, the hemoglobin concentration in the sample for evaluation of storage stability according to the present invention prepared by contacting silica gel with a pseudo-feces with each other to store the pseudo-feces in silica gel was almost 100% even after storage at 50° C. for 5 days. Therefore, it was found that the storage of a feces sample in a dried state in silica gel by contacting a feces sample with silica gel and drying the feces sample stabilizes the feces sample, stabilizes hemoglobin in the feces sample, and holds hemoglobin in the feces sample stably even after storage at 50° C. for 5 days.

Example 2

Stability of Hemoglobin in Pseudo-Feces (2)—Study with Feces Sampling Container Filled with Silica Gel (1) Preparation of Pseudo-Feces A pseudo-feces prepared in (1) in Example 1 was used.

(2) Preparation of Feces Sampling Container Filled with Silica Gel

A feces sampling container filled with silica gel was prepared by filling a feces container chamber of the HEMO-AUTO MC feces sampling container with 200 mg of silica gel instead of Liquid N for suspending feces.

(3) Preparation of Pseudo-Feces Sample (3-1) Pseudo-Feces Sample for Control

The pseudo-feces prepared in above (1) was collected using a feces sampling stick, a component of HEMO-AUTO MC feces sampling container. The feces sampling stick holding the collected pseudo-feces was inserted in the main body of the HEMO-AUTO MC feces sampling container while being rotated and pushed down, and the pseudo-feces was dissolved in a liquid for suspending feces in the HEMO-AUTO MC feces sampling container to prepare Pseudo-feces sample $2_{(control:\ for\ 0\ days)}$.

(3-2) Pseudo-Feces Sample According to the Present Invention

The pseudo-feces prepared in above (1) was collected using a feces sampling stick, a component of HEMO-AUTO MC feces sampling container. The feces sampling stick holding the collected pseudo-feces was inserted in a main body of the feces sampling container filled with silica gel prepared in above (2) while being rotated and pushed down. Silica gel and the pseudo-feces were mixed in a feces container chamber sufficiently to prepare Pseudo-feces sample $2_{(the\ present\ invention:\ for\ 0\ days)}$.

(4) Preparation of Sample for Evaluation of Storage Stability (4-1) Preparation of Control Sample for Evaluation of Storage Stability Pseudo-feces sample $2_{(control:\ for\ 0\ days)}$ prepared in above (3-1) was stored in an incubator at 40° C. for 24 hours to prepare Pseudo-feces sample $2_{(control:\ for\ 1\ day)}$. Similarly, Pseudo-feces sample $2_{(control:\ for\ 0\ days)}$ was stored in an incubator at 40° C. for 6 days to prepare Pseudo-feces sample $2_{(control:\ for\ 6\ days)}$. Similarly, Pseudo-feces sample $2_{(control:\ for\ 0\ days)}$ was stored in an incubator at 40° C. for 10 days to prepare Pseudo-feces sample $2_{(control:\ for\ 10\ days)}$ Each of the prepared Pseudo-feces sample $2_{(control:\ for\ 0\ days)}$, Pseudo-feces sample $2_{(control:\ for\ 1\ day)}$, Pseudo-feces sample $2_{(control:\ for\ 6\ days)}$, and Pseudo-feces sample $2_{(control:\ for\ 10\ days)}$ was used as a control sample for evaluation of storage stability [Sample $2_{(control:\ for\ 0\ days)}$ for evaluation of storage stability; Sample $2_{(control:\ for\ 1\ day)}$ for evaluation of storage stability; Sample $2_{(control:\ for\ 6\ days)}$ for evaluation of storage stability; Sample $2_{(control:\ for\ 10\ days)}$ for evaluation of storage stability].

(4-2) Preparation of Sample for Evaluation of Storage Stability According to the Present Invention Pseudo-feces sample $2_{(the\ present\ invention:\ for\ 0\ days)}$ prepared in above (3-2) was stored in an incubator at 40° C. for 24 hours to prepare Pseudo-feces sample $2_{(the\ present\ invention:\ for\ 1\ day)}$. Similarly, Pseudo-feces sample $2_{(the\ present\ invention:\ for\ 0\ days)}$ was stored in an incubator at 40° C. for 6 days to prepare Pseudo-feces sample $2_{(the\ present\ invention:\ for\ 6\ days)}$. Similarly, Pseudo-feces sample $2_{(the\ present\ invention:\ for\ 0\ days)}$ was stored in an incubator at 40° C. for 10 days to prepare Pseudo-feces sample $2_{(the\ present\ invention:\ for\ 10\ days)}$.

The feces sampling stick was pulled out from the container body of each of the feces sampling containers containing each of the prepared pseudo-feces samples according to the present invention, and Liquid N for suspending feces (2 mL) for HEMO-AUTO MC was added to the feces container chamber. After the feces sampling stick was inserted in the container body, the container body was stirred with a vortex mixer for 1 minute to stir silica gel containing a pseudo-feces and Liquid N for suspending feces in each feces sampling container. After stirring, each of the feces sampling containers was left to stand, and the supernatant in each of the feces sampling containers was collected as a sample for evaluation of storage stability according to the present invention [Sample $2_{(the\ present\ invention:\ for\ 0\ days)}$ for evaluation of storage stability; Sample $2_{(the\ present\ invention:\ for\ 1\ day)}$ for evaluation of storage stability; Sample $2_{(the\ present\ invention:\ for\ 6\ days)}$ for evaluation of storage stability, Sample $2_{(the\ present\ invention:\ for\ 10\ days)}$ for evaluation of storage stability].

(5) Measurement of Hemoglobin in Sample for Evaluation of Storage Stability (5-1) Measurement of Hemoglobin in Control Sample for Evaluation of Storage Stability Except that a control sample for evaluation of storage stability prepared in above (4-1), that is, each of Sample $2_{(control:\ for\ 0\ days)}$ for evaluation of storage stability; Sample $2_{(control:\ for\ 1\ day)}$ for evaluation of storage stability; Sample $2_{(control:\ for\ 6\ days)}$ for evaluation of storage stability; and Sample $2_{(control:\ for\ 10\ days)}$ for evaluation of storage stability was used as a sample for evaluation of storage stability, the hemoglobin concentration in each of the samples for evaluation of storage stability was determined by a method similar to that of (5-1) in Example 1. The hemoglobin concentration in each of the control samples for evaluation of storage stability relative to the hemoglobin concentration in Control Sample $2_{(control:\ for\ 0\ days)}$ for evaluation of storage stability, defined to be 100, is illustrated in Table 2 and FIG. 8.

(5-2) Measurement of Hemoglobin in Sample for Evaluation of Storage Stability According to the Present Invention Except that a sample for evaluation of storage stability according to the present invention prepared in above (4-2), that is, each of Sample $2_{(the\ present\ invention:\ for\ 0\ days)}$ for evaluation of storage stability, Sample $2_{(the\ present\ invention:\ for\ 1\ day)}$ for evaluation of storage stability, Sample$_{(the\ present\ invention:\ for\ 6\ days)}$ for evaluation of storage stability, and Sample $2_{(the\ present\ invention:\ for\ 10\ days)}$ for evaluation of storage stability was used as a sample for evaluation of storage stability instead of a control sample for evaluation of storage stability, the hemoglobin concentration in each of the samples for evaluation of storage stability was determined by a method similar to that of (5-1) in Example 1. The hemoglobin concentration in each of the samples for evaluation of storage stability relative to the hemoglobin concentration in Sample $2_{(the\ present\ invention:\ for\ 0\ days)}$ for evaluation of storage stability, defined to be 100, is illustrated in Table 2 and FIG. 8.

TABLE 2

| Days of storage (Days) | Hemoglobin concentration in sample for evaluation of storage stability (%) | |
| --- | --- | --- |
| | Present invention | Control |
| 0 | 100 | 100 |
| 1 | 98 | 38 |
| 6 | 98 | 4 |
| 10 | 83 | 4 |

As apparent from Table 2 and FIG. 8, while the hemoglobin concentration in the control sample for evaluation of storage stability prepared by dissolving a pseudo-feces in Liquid N for suspending feces in the feces sampling container was decreased to 38% after storage at 40° C. only for 1 day, the hemoglobin concentration in the sample for evaluation of storage stability according to the present invention prepared by dissolving a pseudo-feces in Liquid N for suspending feces in the feces sampling container was almost 100% even after storage at 40° C. for 6 days and 80% or more even after storage at 40° C. for 10 days. Therefore, it was found that the storage of a feces sample in a dried state in silica gel by contacting the feces sample with silica gel and drying the feces sample stabilizes the feces sample, stabilizes hemoglobin in the feces sample, and holds hemoglobin in the feces sample stably even after storage at 40° C. for 6 days or more.

Example 3

Stability of Hemoglobin in Real Feces—Study with Container Filled with Silica Gel (1) Preparation of Real Feces A cryopreserved positive feces originated from a human was thawed by leaving it to stand at 25° C. for 1 hour and stirred with a stirring stick uniformly to prepare a real feces. Here, the positive feces is a feces having 30 µg or more of hemoglobin per 1 g of feces.

(2) Preparation of Container Filled with Silica Gel

A screw cap Spitz tube (10 mL, manufactured by Eiken Chemical Co., Ltd.) was filled with 1.4 g of silica gel to prepare a container filled with silica gel.

(3) Preparation of Real Feces Sample (3-1) Real Feces Sample for Control

The real feces prepared in above (1) was collected using a feces sampling stick, a component of HEMO-AUTO MC feces sampling container. The feces sampling stick holding the collected real feces was inserted in the main body of the HEMO-AUTO MC feces sampling container while being rotated and pushed down, and the real feces was dissolved in Liquid N for suspending feces in the HEMO-AUTO MC feces sampling container to prepare Real feces sample$_{(control:\ for\ 0\ days)}$.

(3-2) Real Feces Sample According to the Present Invention

The real feces prepared in above (1) was collected using a feces sampling stick, a component of HEMO-AUTO MC feces sampling container. The collected real feces was directly inserted in a leveling hole of a lower fitting block (separator) [see Patent Document 1 stated above (40 in FIG. 9)], a component of the HEMO-AUTO MC feces sampling container, and excess real feces attached to the feces sampling stick was removed. Subsequently, a tip part (a part up to approximately 2 cm from the tip) of the feces sampling stick after excess real feces was removed was cut with a nipa and added to the screw cap Spitz tube of above (2). Then, the screw cap Spitz tube containing the tip part of the feces sampling stick holding the real feces was closed with the screw cap. The screw cap Spitz tube was stirred sufficiently to mix the real feces with silica gel in the screw cap Spitz tube and to prepare Real feces sample$_{(the\ present\ invention:\ for\ 0\ days)}$.

(4-1) Preparation of Control Sample for Evaluation of Storage Stability

Real feces sample$_{(control:\ for\ 0\ days)}$ prepared in above (3-1) was stored in an incubator at 40° C. for 24 hours to prepare Real feces sample$_{(control:\ for\ 1\ day)}$. Similarly, Real feces sample$_{(control:\ for\ 0\ days)}$ was stored in an incubator at 40° C. for 2 days to prepare Real feces sample$_{(control:\ for\ 2\ days)}$. Similarly, Real feces sample$_{(control:\ for\ 0\ days)}$ was stored in an incubator at 40° C. for 3 days to prepare Real feces sample$_{(control:\ for\ 3\ days)}$. Similarly, Real feces sample$_{(control:\ for\ 0\ days)}$ was stored in an incubator at 40° C. for 5 days to prepare Real feces sample$_{(control:\ for\ 5\ days)}$. Each of prepared Real feces sample$_{(control:\ for\ 0\ days)}$, Real feces sample$_{(control:\ for\ 1\ day)}$, Real feces sample$_{(control:\ for\ 2\ days)}$, Real feces sample$_{(control:\ for\ 3\ days)}$, Real feces sample$_{(control:\ for\ 5\ days)}$ was used as a control sample for evaluation of storage stability [sample $3_{(control:\ for\ 0\ days)}$ for evaluation of storage stability; sample $3_{(control:\ for\ 1\ day)}$ for evaluation of storage stability; sample $3_{(control:\ for\ 2\ days)}$ for evaluation of storage stability; sample $3_{(control:\ for\ 3\ days)}$ for evaluation of storage stability; sample $3_{(control:\ for\ 5\ days)}$ for evaluation of storage stability].

(4-2) Preparation of Sample for Evaluation of Storage Stability According to the Present Invention Real feces sample$_{(the\ present\ invention:\ for\ 0\ days)}$ prepared in above (3-2) was stored in an incubator at 40° C. for 24 hours to prepare Real feces sample$_{(the\ present\ invention:\ for\ 1\ day)}$. Similarly, Real feces sample$_{(the\ present\ invention:\ for\ 0\ days)}$ was stored in an incubator at 40° C. for 2 days to prepare Real feces sample$_{(the\ present\ invention:\ for\ 2\ days)}$. Similarly, Real feces sample$_{(the\ present\ invention:\ for\ 0\ days)}$ was stored in an incubator at 40° C. for 3 days to prepare Real feces sample$_{(the\ present\ invention:\ for\ 3\ days)}$. Similarly, Real feces sample$_{(the\ present\ invention:\ for\ 0\ days)}$ was stored in an incubator at 40° C. for 5 days to prepare Real feces sample$_{(the\ present\ invention:\ for\ 5\ days)}$.

Liquid N for suspending feces (4 mL) contained in the HEMO-AUTO MC feces sampling container was added to each of the screw cap Spitz tubes containing each of the prepared real feces sample according to the present invention. Subsequently, the screw cap Spitz tubes were closed with screw caps and each of the screw cap Spitz tubes was stirred with a vortex mixer for 1 minute to mix silica gel holding real feces with Liquid N for suspending feces in each of the screw cap Spitz tubes. After stirring, each of the screw cap Spitz tubes was left to stand, and the supernatant in each of the screw cap Spitz tubes was collected as a sample for evaluation of storage stability according to the present invention [Sample $3_{(the\ present\ invention:\ for\ 0\ days)}$ for evaluation of storage stability; Sample $3_{(the\ present\ invention:\ for\ 1\ day)}$ for evaluation of storage stability; Sample $3_{(the\ present\ invention:\ for\ 2\ days)}$ for evaluation of storage stability; Sample $3_{(the\ present\ invention:\ for\ 3\ days)}$ for evaluation of storage stability; Sample $3_{(the\ present\ invention:\ for\ 5\ days)}$ for storage evaluation of stability].

(5) Measurement of Hemoglobin in Sample for Evaluation of Storage Stability (5-1) Measurement of Hemoglobin in Control Sample for Evaluation of Storage Stability Except that a control sample for evaluation of storage stability prepared in (4-1) above, that is, each of Sample $3_{(control:\ for\ 0\ days)}$ for evaluation of storage stability; Sample $3_{(control:\ for\ 1\ day)}$ for evaluation of storage stability; Sample $3_{(control:\ for\ 2\ days)}$ for evaluation of storage stability, Sample $3_{(control:\ for\ 3\ days)}$ for evaluation of storage stability; and Sample $3_{(control:\ for\ 5\ days)}$ for evaluation of storage stability was used as a sample for evaluation of storage stability, the hemoglobin concentration in each of the control samples for evaluation of storage stability was determined by a method similar to that of (5-1) in Example 1. The hemoglobin concentration in each of the control samples for evaluation of storage stability relative to the hemoglobin concentration in Control Sample $3_{(control:\ for\ 0\ days)}$ for evaluation of storage stability, defined to be 100, is illustrated in Table 3 and FIG. 9.

(5-2) Measurement of Hemoglobin in Sample for Evaluation of Storage Evaluation According to the Present Invention Except that a sample for evaluation of storage stability according to the present invention prepared in above (4-2), that is, each of Sample $3_{(the\ present\ invention:\ for\ 0\ days)}$ for evaluation of storage stability, Sample $3_{(the\ present\ invention:\ for\ 1\ day)}$ for evaluation of storage stability, Sample$_{(the\ present\ invention:\ for\ 2\ days)}$ for evaluation of storage stability, Sample $3_{(the\ present\ invention:\ for\ 3\ days)}$ for evaluation of storage stability, Sample $3_{(the\ present\ invention:\ for\ 4\ days)}$ for evaluation of storage stability, and Sample $3_{(the\ present\ invention:\ for\ 5\ days)}$ for evaluation of storage stability was used as a sample for evaluation of storage stability instead of a control sample for evaluation of storage stability, the hemoglobin concentration in each of the samples for evaluation of storage stability was determined by a method similar to that of (5-1) in Example 1. The hemoglobin concentration in each of the samples for evaluation of storage stability relative to the hemoglobin concentration in Sample$_{(the\ present\ invention:\ for\ 0\ days)}$ for evaluation of storage stability defined to be 100 is illustrated in Table 3 and FIG. 9.

TABLE 3

| Days of storage (Days) | Hemoglobin concentration in sample for evaluation of storage stability (%) | |
|---|---|---|
| | Present invention | Control |
| 0 | 100 | 100 |
| 1 | 56 | 9 |
| 2 | 51 | 6 |
| 3 | 46 | 7 |
| 5 | 36 | 3 |

As apparent from Table 3 and FIG. 9, while the hemoglobin concentration in the control sample for evaluation of storage stability prepared by dissolving a real feces in Liquid N for suspending feces was decreased to 9% after storage at 40° C. only for 1 day, the hemoglobin concentration in the sample for evaluation of storage stability according to the present invention prepared by contacting silica gel and a real feces with each other to store the real feces in silica gel was 40% or more even after storage at 40° C. for 3 days. Therefore, it was found that, even when a real feces was used as a feces sample, the storage of the feces sample in a dried state in silica gel by contacting the feces sample with silica gel to dry the feces sample stabilizes the feces sample, stabilizes hemoglobin in the feces sample, and holds hemoglobin in the feces sample stably even after storage at 40° C. for 3 days.

Example 4

Stability of Hemoglobin in Pseudo-Feces (3)—Study Using Container Filled with Aluminum Oxide
(1) Preparation of Pseudo-Feces
A pseudo-feces prepared in (1) in Example 1 was used.
(2) Preparation of Container Filled with Aluminum Oxide
A screw cap Spitz tube (10 mL, manufactured by Eiken Chemical Co., Ltd.) was filled with 200 mg of aluminum oxide to prepare a container filled with aluminum oxide.
(3) Preparation of Pseudo-Feces Sample
(3-1) Pseudo-Feces Sample for Control
The pseudo-feces prepared in above (1) was collected using a feces sampling stick, a component of HEMO-AUTO MC feces sampling container. The feces sampling stick holding the collected pseudo-feces was inserted in the main body of the HEMO-AUTO MC feces sampling container while being rotated and pushed down, and the pseudo-feces was dissolved in Liquid N for suspending feces in the HEMO-AUTO MC feces sampling container to prepare Pseudo-feces sample $3_{(control:\ for\ 0\ days)}$.
(3-2) Pseudo-Feces Sample According to the Present Invention
The pseudo-feces prepared in above (1) was collected using a feces sampling stick, a component of HEMO-AUTO MC feces sampling container. The collected pseudo-feces was directly inserted in a leveling hole of a lower fitting block (separator) [see Patent Document 1 stated above (40 in FIG. 9)], a component of the HEMO-AUTO MC feces sampling container, and excess pseudo-feces attached to the feces sampling stick was removed. Subsequently, a tip part (a part up to approximately 2 cm from the tip) of the feces sampling stick after excess pseudo-feces was removed was cut with a nipa and added to the screw cap Spitz tube of above (2). Then, the screw cap Spitz tube containing the tip part of the feces sampling stick holding the Pseudo-feces was closed with the screw cap. The screw cap Spitz tube was stirred sufficiently to mix the pseudo-feces with aluminum oxide in the screw cap Spitz tube to prepare Pseudo-feces sample $3_{(the\ present\ invention:\ for\ 0\ days)}$.
(4) Preparation of Sample for Evaluation of Storage Stability
(4-1) Preparation of Control Sample for Evaluation of Storage Stability
Pseudo-feces sample $3_{(control:\ for\ 0\ days)}$ prepared in above (3-1) was stored in an incubator at 40° C. for 24 hours to prepare Pseudo-feces sample $3_{(control:\ for\ 1\ day)}$. Similarly, Pseudo-feces sample $3_{(control:\ for\ 0\ days)}$ was stored in an incubator at 40° C. for 3 days to prepare Pseudo-feces sample $3_{(control:\ for\ 3\ days)}$. Similarly, Pseudo-feces sample 3 (control: for 0 days) was stored in an incubator at 40° C. for 6 days to prepare Pseudo-feces sample $3_{(control:\ for\ 6\ days)}$ Each of prepared Pseudo-feces sample $3_{(control:\ for\ 0\ days)}$, Pseudo-feces sample $3_{(control:\ for\ 1\ day)}$ Pseudo-feces sample $3_{(control:\ for\ 3\ days)}$, and Pseudo-feces sample $3_{(control:\ for\ 6\ days)}$ was used as a control sample for evaluation of storage stability [Sample $3_{(control:\ for\ 0\ days)}$ for evaluation of storage stability; Sample $3_{(control:\ for\ 1\ day)}$ for evaluation of storage stability; Sample $3_{(control:\ for\ 3\ days)}$ for evaluation of storage stability, Sample $3_{(control:\ for\ 6\ days)}$ for evaluation of storage stability].
(4-2) Preparation of Sample for Evaluation of Storage Stability According to the Present Invention
Pseudo-feces sample $3_{(the\ present\ invention:\ for\ 0\ days)}$ prepared in above (3-2) was stored in an incubator at 40° C. for 24 hours to prepare Pseudo-feces sample $3_{(the\ present\ invention:\ for\ 1\ day)}$. Similarly, Pseudo-feces sample $3_{(the\ present\ invention:\ for\ 0\ days)}$ was stored in an incubator at 40° C. for 3 days to prepare Pseudo-feces sample $3_{(the\ present\ invention:\ for\ 3\ days)}$. Similarly, Pseudo-feces sample $3_{(the\ present\ invention:\ for\ 0\ days)}$ was stored in an incubator at 40° C. for 6 days to prepare Pseudo-feces sample $3_{(the\ present\ invention:\ for\ 6\ days)}$.
Liquid N for suspending feces (4 mL) contained in the HEMS AUTO MC feces sampling container was added to each of the screw cap Spitz tubes containing each of the prepared pseudo-feces samples according to the present invention. Subsequently, the screw cap Spitz tubes were closed with screw caps and each of the screw cap Spitz tubes was stirred with a vortex mixer for 1 minute to mix aluminum oxide holding the pseudo-feces with Liquid N for suspending feces in each screw cap Spitz tube. After stirring, each of the screw cap Spitz tubes was left to stand, and the supernatant in each of the screw cap Spitz tubes was collected as a sample for evaluation of storage stability according to the present invention [Sample $4_{(the\ present\ invention:\ for\ 0\ days)}$ for evaluation of storage stability; Sample $4_{(the\ present\ invention:\ for\ 1\ day)}$ for evaluation of storage stability; Sample $4_{(the\ present\ invention:\ for\ 3\ days)}$ for evaluation of storage stability; Sample $4_{(the\ present\ invention:\ for\ 6\ days)}$ for evaluation of storage stability].
(5) Measurement of Hemoglobin in Sample for Evaluation of Storage Stability
(5-1) Measurement of Hemoglobin in Control Sample for Evaluation of Storage Stability
Except that a control sample for evaluation of storage stability prepared in above (4-1), that is, each of Sample $4_{(control:\ for\ 0\ days)}$ for evaluation of storage stability; Sample $4_{(control:\ for\ 1\ day)}$ for evaluation of storage stability; Sample $4_{(control:\ for\ 3\ days)}$ for evaluation of storage stability, and Sample $4_{(control:\ for\ 6\ days)}$ for evaluation of storage stability was used as a sample for evaluation of storage stability, the hemoglobin concentration in each of the control samples for evaluation of storage stability was determined by a method similar to that of (5-1) in Example 1. The hemoglobin concentration in each of the control samples for evaluation of storage stability relative to the hemoglobin concentration in Control Sample $4_{(control:\ for\ 0\ days)}$ for evaluation of storage stability, defined to be 100, is illustrated in Table 4 and FIG. 10.

(5-2) Measurement of Hemoglobin in Sample for Evaluation of Storage Stability According to the Present Invention Except that a sample for evaluation of storage stability according to the present invention prepared in above (4-2), that is, each of Sample $4_{(the\ present\ invention:\ for\ 0\ days)}$ for evaluation of storage stability, Sample $4_{(the\ present\ invention:\ for\ 1\ day)}$ for evaluation of storage stability, Sample $4_{(the\ present\ invention:\ for\ 3\ days)}$ for evaluation of storage stability, and Sample $4_{(the\ present\ invention:\ for\ 6\ days)}$ for evaluation of storage stability was used as a sample for evaluation of storage stability instead of a control sample for evaluation of storage stability, the hemoglobin concentration in each of the samples for evaluation of storage stability was determined by a method similar to that of (5-1) in Example 1. The hemoglobin concentration in each of the samples for evaluation of storage stability relative to the hemoglobin concentration in Sample $4_{(the\ present\ invention:\ for\ 0\ days)}$ for evaluation of storage stability, defined to be 100, is illustrated in Table 4 and FIG. 10.

TABLE 4

| Days of storage (Days) | Hemoglobin concentration in sample for evaluation of storage stability (%) | |
|---|---|---|
| | Present invention | Control |
| 0 | 100 | 100 |
| 1 | 77 | 40 |
| 3 | 66 | 7 |
| 6 | 50 | 1 |

As apparent from Table 4 and FIG. 10, while the hemoglobin concentration in the control sample for evaluation of storage stability prepared by dissolving a pseudo-feces in Liquid N for suspending feces was decreased to 40% after storage at 40° C. only for 1 day, the hemoglobin concentration in the sample for evaluation of storage stability according to the present invention prepared by contacting aluminum oxide with a pseudo-feces with each other to store the pseudo-feces in aluminum oxide was 60% or more even after storage at 40° C. for 3 days and 50% or more even after storage at 40° C. for 6 days. Therefore, it was found that the storage of a feces sample in a dried state in aluminum oxide by contacting the feces sample with aluminum oxide and drying the feces sample stabilizes the feces sample, stabilizes hemoglobin in the feces sample, and holds hemoglobin in the feces sample stably even after storage at 40° C. for 3 days.

INDUSTRIAL APPLICABILITY

The present invention is useful in the field of medical instruments and medical devices, since by using a feces sampling container according to the present invention and a method for stabilizing a component in a feces sample according to the present invention, a component in a feces sample can be stabilized to give an accurate measurement/detection of a component in a feces sample.

EXPLANATION OF LETTERS OR NUMERALS 1 feces sampling container
2 feces sampling stick
3 gripping part
4 hollow part in gripping part
5 feces sampling part
6 base end (screw part)
7 stick part
8 pierce part
9 top face of gripping part
10 fitting body
11 first leveling part (hole)
12 second leveling part (hole)
13 tubular guide part
14 pierce part
20 bottomed tubular container body
21 feces container chamber (desiccant storage chamber)
22 pierce part
30 tube container body
31 feces container chamber (desiccant storage chamber)
32 trunk part
33 sealed bottom part
B feces sample
$B_D$ feces sample in dried state
D desiccant

The invention claimed is:

1. A feces sampling container comprising: a container body, and a feces sampling stick having a gripping part on one side and a stick part on the other side, the stick part having a feces sampling part in the vicinity of the tip thereof, wherein the container body comprises: an opening part through which the feces sampling part of the feces sampling stick is inserted, and a feces container chamber in which a desiccant in a powder form is enclosed therein, wherein the feces sample held by the feces sampling part is dried by directly physically contacting the feces sampling part, which is inserted through the opening part and holding the feces sample, with the desiccant in a powder form, and the feces sample in a dried state is stored in the desiccant.

2. The feces sampling container according to claim 1, wherein the opening part comprises a leveling hole for removing excess feces.

3. The feces sampling container according to claim 1, wherein the feces container chamber is formed with a fitting body fitted in the container body.

4. The feces sampling container according to claim 3, wherein the fitting body is comprised of an upper fitting block and a lower fitting block.

5. The feces sampling container according to claim 1, wherein a bottom of the container body comprises a pierce part for introducing an aqueous medium for dissolving a component in the feces sample.

6. The feces sampling container according to claim 3, wherein the fitting body comprises a pierce part for introducing an aqueous medium for dissolving a component in the feces sample in a top part thereof.

7. The feces sampling container according to claim 1, wherein the desiccant is a physical desiccant.

8. The feces sampling container according to claim 7, wherein the physical desiccant is silica gel or aluminum oxide.

9. A method for measuring a component in a feces sample, comprising: directly physically contacting a collected feces sample with a desiccant in a powder form to dry the feces sample; storing the feces sample in a dried state in the desiccant; adding an aqueous medium to the desiccant, in which the feces sample in the dried state, is stored to dissolve the component in the feces sample in the aqueous medium; and measuring the component in the feces sample dissolved in the aqueous medium.

10. The method for measuring according to claim 9, wherein the desiccant is a physical desiccant.

11. The method for measuring according to claim 10, wherein the physical desiccant is silica gel or aluminum oxide.

12. The method for measuring according to claim 9, wherein the component in the feces sample is hemoglobin.

13. A method for stabilizing a component in a feces sample, comprising directly physically contacting a collected feces sample with a desiccant in a powder form to dry the feces sample; and storing the feces sample in a dried state in the desiccant.

14. The method for stabilizing according to claim 13, wherein the desiccant is a physical desiccant.

15. The method for stabilizing according to claim 14, wherein the physical desiccant is silica gel or aluminum oxide.

16. The method for stabilizing according to claim 13, wherein the component in the feces sample is hemoglobin.

17. A method for storing a feces sample, comprising directly physically contacting a collected feces sample with a desiccant in a powder form to dry the feces sample; and storing the feces sample in a dried state in the desiccant.

18. The method according to claim 17, wherein the desiccant is a physical desiccant.

19. The method according to claim 18, wherein the physical desiccant is silica gel or aluminum oxide.

* * * * *